(12) United States Patent
Pohlschroder et al.

(10) Patent No.: US 7,447,595 B1
(45) Date of Patent: Nov. 4, 2008

(54) HETEROLOGOUS PROTEIN PRODUCTION USING THE TWIN ARGININE TRANSLOCATION PATHWAY

(75) Inventors: Mechtild Pohlschroder, Philadelphia, PA (US); Jessica C Kissinger, Athens, GA (US); R. Wesley Rose, Glenside, PA (US); Thomas Brueser, Halle (DE); Kieran Dilks, Collingswood, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 153 days.

(21) Appl. No.: 10/507,855

(22) PCT Filed: Mar. 17, 2003

(86) PCT No.: PCT/US03/08161

§ 371 (c)(1),
(2), (4) Date: Jun. 21, 2005

(87) PCT Pub. No.: WO03/079007

PCT Pub. Date: Sep. 25, 2003

Related U.S. Application Data

(60) Provisional application No. 60/441,576, filed on Jan. 21, 2003, provisional application No. 60/364,877, filed on Mar. 15, 2002.

(51) Int. Cl.
*G01N 33/48* (2006.01)
*A61K 38/06* (2006.01)
*A61K 38/16* (2006.01)

(52) U.S. Cl. .............................. 702/19; 703/11; 435/7.1; 530/330; 530/350

(58) Field of Classification Search ........................ None
See application file for complete search history.

(56) References Cited

U.S. PATENT DOCUMENTS 6,022,952 A * 2/2000 Weiner et al. ................ 530/350

OTHER PUBLICATIONS

Altschul et al., *J. Molecular Biology*, vol. 215, No. 3, pp. 403-410 (Oct. 1990).
Altschul et al., "Gapped BLAST and PSI-BLAST: A New Generation of Protein Database Search Programs," *Nucleic Acids Research*, vol. 25, No. 17, pp. 3389-3402, (1997).
Bender et al., *Applied Microbiol. Biotechnol.*, vol. 34, Issue 2, pp. 203-207, (1990).
Bentley et al., Complete Genome Sequence of the Model Actinomycete Streptomyces Coelicolor (A3(2)), *Nature*, vol. 417, pp. 141-147 (2002).
Berks, "A Common Export Pathway for Proteins Binding Complex Redox Cofactors?," *Molecular Microbiology*, vol. 22, Issue 3, pp. 393-404 (Nov. 1996).
Berks et al., "The Tat Protein Export Pathway," *Molecular Microbiology*, vol. 35, No. 2, pp. 260-274 (2000).

Bogsch et al., "An Essential Component of a Novel Bacterial Protein Export System with Homologues in Plastics and Mitochondria," *J. of Biological Chemisty*, vol. 273, No. 29, pp. 18003-18006 (1998).
Brink et al., "Targeting of Thylakoid Proteins by the ΔpH-Driven Twin-Arginine Translocation Pathway Requires a Specific Signal in the Hydrophobic Domain in Conjunction with the Twin-Arginine Motif." *FEBS Letters*, vol. 434, pp. 425-430 (1998).
Chaddock et al., "A New Type of Signal Peptide: Central Role of a Twin-Arginine Motif in Transfer Signals for tje ΔpH-Dependent Thylakoidal Protein Translocase", *EMBO J.*, vol. 14, pp. 2715-2722 (1995).
Chang et al., In Biology of Actinomycetes '88, "Proc. of Seventh International Symposium on Biology of Actinomycetes" *Japanese Sci. Soc. Press*, Tokyo, pp. 103-107 (1988).
Cid et al., "Hydrophobicity and Structural Classes in Proteins," *Protein Engineering*, vol. 5, No. 5, pp. 373-375, Oxford University Press (1992).
Cline et al., "Transformation of the Archaebacterium *Halobacterium volcanii* with Genomic DNA," *J. of Bacteriology*, vol. 171, No. 9, pp. 4987-4991, (Sep. 1989).
Cline et al., "Protein-specific Energy Requirements for Protein Transport Across or into Thylakoid Membranes," *J. Biological Chemistry*, vol. 267, No. 4, pp. 2688-2696 (1992).
Cristobal et al., "Competition Between Sec- and TAT-Dependent Protein Translocation in *Escherichia coli*," *The EMBO J.*, vol. 18, No. 11, pp. 2982-2990 (1999).
Dilks et al., "Prokaryotic Utilization of the Twin-Arginine Translocation Pathway: a Genomic Survey," *J. Bacteriology*, vol. 185, No. 4, pp. 1478-1483 (Feb. 2003).
Engles et al., *Transgenesis—Application of Gene Transfer*, (Murray, ed.), Wiley & Sons, pp. 32-53 (1992).
Fekkes et al., "Protein Targeting to the Bacterial Cytoplasmic Membrane," *Microbiology and Molecular Biology Reviews*, vol. 63, No. 1, pp. 161-173, (Mar. 1999).
Gilbert et al., "Production and Secretion of Proteins by Streptomyces," *Crit. Rev. Biotechnol.*, vol. 15, No. 1, pp. 13-39 (1995).
Hynds et al., "The Sec-Independent Twin-Arginine Translocation System can Transport Both Tightly Folded and Malfolded Proteins Across the Thylakoid Membrane," *J Biological Chemistry*, vol. 273, No. 52, pp. 34868-34874 (1998).
Jongbloed et al., "TatC Is a Specificity Determinant for Protein Secretion via the Twin-Arginine Translocation Pathway," *J. Biological Chemistry*, vol. 275, No. 52, pp. 41350-41357 (2000).

(Continued)

*Primary Examiner*—Michael Borin
(74) *Attorney, Agent, or Firm*—Evelyn H. McConathy; Montgomery, McCracken, Walker & Rhoads, LLP

(57) ABSTRACT

Provided are means for evaluating and identifying putative substrates of the twin arginine translocation (Tat) secretory pathway in *Streptomyces* and other bacterial species. Also provided, therefore, are simple ways to express, secrete and purify correctly folded heterologous proteins on a large scale using host microorganisms, such as, *Streptomyces* and the Tat pathway therein. Many of the thus-produced proteins are of significant therapeutic value in the pharmaceutical and biochemical industries, particularly when they can be secreted from the host in fully-folded active form. Accordingly, there are further provided the heterologous proteins produced by the Tat secretion pathway using the foregoing methods, and the computer algorithm used to identify the Tat signal sequence and putative substrates.

3 Claims, 2 Drawing Sheets

OTHER PUBLICATIONS

Kobayashi et al., "Cloning, Expression and Nucleotide Sequence of the α-Amaylase Gene from the Haloalkaliphilic Archaeon Natronococcus sp. Strain Ah-36," *J. Bacteriology*, vol. 176, No. 16, pp. 5131-5134 (Aug. 1994).

Matlack et al., "Protein Translocation Tunnel Vision," *Cell*, vol. 92, pp. 381-390 (Feb. 1998).

Mori et al., "The Sec Protein-Translocation Pathway," *Trends in Microbiology*, vol. 9, Issue 10, pp. 494-500 (Oct. 2001).

Molnar et al., "Recombinant Microbes for Industrial and Agricultural Applicaitons," (Murooka and Imanaka, eds.) Marcel Dekker, Inc., pp. 81-104 (1994).

Nielsen et al., "Identification of Prokaryotic and Eukaryotic Signal Peptides and Predication of Their Cleavage Sites," *Protein Engineering*, vol. 10, No. 1, pp. 1-6 (1997).

Niviere et al., "Site-directed Mutagenesis of the Hydrogenase Signal Peptide Consensus Box Prevents Export of a β-lactamase Fusion Protein," *J. General Microbiology*, vol. 138, pp. 2173-2183 (1992).

Noack et al., "Expression and Secretion of Interferon-β1 by Streptomyces lividans: Use of Staphylokinase Signals and Amplification of a Neo Gene," *Gene*, vol. 68, Issue 1, pp. 53-62, (Aug. 1988).

Ochsner et al., "Effects of the Twin-Arginine Translocase on Secretion of Virulence Factors, Stress Response, and Pathogenesis," *Proceeding of the National Academy of Sciences of the United States of America*, vol. 99, No. 12, pp. 8312-8317 (Jun. 2002).

Pohlschröder et al., "Protein Translocation in the Three Domains of Life: Variations on a Theme," *Cell*, vol. 91, pp. 563-566 (Nov. 1997).

Robinson et al., "Protein Targeting by the Twin-Arginine Translocation Pathway," *Nat. Rev. Mol. Cell Biol.*, vol. 2, No. 5, pp. 350-356 (2001).

Rodrigue et al., "Co-Translocation of a Periplasmic Enzyme Complex by a Hitchhiker Mechanism Through the Bacterial Tat Pathway," *J. Biological Chemistry*, vol. 274, No. 19, pp. 13223-13228 (1999).

Rose et al., "Adaptation of Protein Secretion to Extremely High-Salt Conditions by Extensive Use of the Twin-Arginine Translocation Pathway," *Molecular Microbiology*, vol. 4, No. 4, pp. 943-950 (2002).

Rowland et al., "The Effect of Signal Sequences on the Efficiency of Secretion of a Heterologous Phosphotriesterase by *Streptomyces lividans*," *Appl Microbiol. Biotechnol*, vol. 38, pp. 94-100 (1992).

Santini et al., "A Novel sec-Independent Periplasmic Protein Translocation Pathway in *Escherichia coli*," *The EMBO J.*, vol. 17, No. 1, pp. 101-112 (1998).

Sargent et al., "Overlapping Functions of Components of a Bacterial Sec-Independent Protein Export Pathway," *The EMBO J.*, vol. 17, No. 13, pp. 3640-3650 (1998).

Sargent et al., "Sec-Independent Protein Translocation in *Escherichia coli*," *J. Biological Chemistry*, vol. 274, No. 51, pp. 36073-36082 (1999).

Schaerlaekens et al., "Twin-Arginine Translocation Pathway in Streptomyces lividans," *J Bacteriology*, vol. 183, No. 23, pp. 6727-6732 (Dec. 2001).

Settles et al., "Sec-Independent Protein Translocation by the Maize Hcf106 Protein," *Science*, vol. 278, pp. 1467-1470 (1997).

Sonnhammer et al., "A Hidden Markov Model for Predicting Transmembrane Helices in Protein Sequences," *Proc. Int. Conf. Intell. Syst. Mol. Biol.*, vol. 6, pp. 175-182 (1998).

Stanley et al., "*Escherichia coli* Strains Blocked in Tat-Dependent Protein Export Exhibit Pleiotropic Defects in the Cell Envelope," *J Bacteriology*, vol. 183, No. 1, pp. 139-144 (Jan. 2001).

Thomas, et al., "Export of active Green Fluorescent Protein to the Periplasm by the Twin-Arginine Translocase (Tat) Pathway in *Escherichia coli*," *Molecular Microbiology*, vol. 39, No. 1, pp. 47-53 (2001).

Voelker et al. "Two Nuclear Mutations Disrupt Distinct Pathways for Targeting Proteins to the Chloroplast Thylakoid," *The EMBO J.*, vol. 14, No. 16, pp. 3905-3914 (1995).

Voulhoux et al., "Involvement of the Twin-Arginine Translocation System in Protein Secretion via the Type II Pathway," *The EMBO J.*, vol. 20, No. 23, pp. 6735-6741 (2001).

Weiner et al., "A Novel and Ubiquitous System for Membrane Targeting and Secretion of Cofactor-Containing Proteins," *Cell*, vol. 93, pp. 93-101 (Apr. 1998).

Wu et al., "Bacterial Twin-Arginine Signal Peptide-Dependent Protein Translocation Pathway: Evolution and Mechanism," *J. Mol. Microbiol. Biotechnol.*, vol. 2, No. 2, pp. 179-189 (2000).

Yen et al., "Sequence and Phylogenetic Analyses of the Twin-Arginine Targeting (Tat) Protein Export System," *Arch Microbiol.*, vol. 177, pp. 441-450 (2002).

\* cited by examiner

HETEROLOGOUS PROTEIN PRODUCTION USING THE TWIN ARGININE TRANSLOCATION PATHWAY

REFERENCE TO RELATED APPLICATION

This application claims priority to U.S. Provisional Application Nos. 60/364,877, filed Mar. 15, 2002, and 60/441,576, filed Jan. 21, 2003, the contents of each of which are herein incorporated by reference.

GOVERNMENT INTEREST

This invention was supported in part by Grant Nos. T32GM-007229 from the National Institutes of Health, 0110093U from the American Heart Association, MCB 9816411 from the National Science Foundation and DE-FG02-01ER15169 from the Department of Energy. Accordingly, the Government may have certain rights in this invention.

FIELD OF THE INVENTION

This invention comprises a method of analyzing a protein secretion process in certain prokaryotic organisms, and methods for achieving the efficient, controlled production of folded heterologous proteins therefrom.

BACKGROUND OF THE INVENTION

Genomics research has led to protein therapeutics that are claiming an increasingly large portion of the therapeutic drug market. Protein-based therapies constitute a growing portion of pharmaceutical and biotechnology pipelines. One of the biggest challenges in heterologous protein production on an industrial scale involves the purification of recombinant proteins. Because the protein concentration in the extra-cytoplasmic environment is drastically lower than in the cytoplasm, and often the secreted recombinant protein is the predominant protein in the supernatant, purification of secreted recombinant proteins from extra-cytoplasmic environment proves to be much easier compared to that from the cytoplam. The secreted recombinant protein can be separated from the cells by simple filtration or protein precipitation techniques. This approach of making recombinant proteins secreted has been extremely valuable for the production of numerous proteins, including insulin, growth hormones, various antibodies, and other immunoglobulins, whereby these recombinant proteins are secreted in an unfolded conformation via the universally conserved and essential general secretion (Sec) pathway (Matlack et al., *Cell* 92:381-390 (1998); Mori et al., *Trends in Microbiology* 9:494-500 (2001); Pohlschroder et al., *Cell* 91:563-566 (1997); Fekkes et al., *Microbiol. Mol. Biol. Rev.* 63:161-173 (1999)).

However, the Sec pathway transports proteins only in an unfolded state, thus it is useless for exporting a significant number of proteins that fold prematurely in the cytoplasm or are unable to fold correctly in the extra-cytoplasmic environment.

Currently, proteins that cannot fold correctly in the extra-cytoplasmic environment must be expressed within the cytoplasm. However, that presents several problems. (i) Proteins folded prior to translocation cannot be secreted into the external environment when fused to a Sec signal sequence. Nevertheless, the Sec signal sequence still targets such folded proteins to the Sec pore, thereby most likely blocking the essential translocation pore, and thus severely affecting host growth. (ii) Purification of heterologously expressed proteins from complex cytoplasmic extracts is extremely challenging and very costly. (iii) Such heterologous proteins are often not stable in the cytoplasmic environment, and tend to aggregate, or be subjected to protein degradation by cytoplasmic proteases. (iv) In some cases cytoplasmically overexpressed proteins form inclusion bodies that are more easily purified, but then resolubilization of such inclusion bodies is often highly challenging and seldom recovers active proteins. Therefore, there is a need for the development of a new method that allows efficient translocation of pre-folded recombinant protein.

Consequently, the focus of the present invention is an alternate secretion mechanism, the twin arginine translocation (Tat) pathway, which secretes proteins in prefolded conformation (Hynds et al., *J. Biol. Chem.* 273:34868-34874 (1998); Rodrigue et al., *J. Biol. Chem.* 274:13223-13228 (1999); Thomas et al., *Mol. Microbiol.* 39:47-53 (2001)). Tat was originally identified in chloroplasts, has since also been found in bacteria and archaea (Santini et al., *EMBO J.* 17:101-112 (1998); Settles, et al., *Science* 278:1467-1470 (1997); Voelker et al., *EMBO J.* 14:3905-3914 (1995); Yen et al., *Arch. Microbiol.* 177:441-450 (2002).

Analyses of Tat mutants and substrates suggested that the major role of this pathway in *Escherichia coli* prokaryotes is to translocate redox proteins that integrate their co-factors in the cytoplasm and, therefore, possess some degree of tertiary structure prior to secretion (Berks, 1996; Rodrigue et al., 1999; Weiner et al., *Cell* 93:93-101 (1998)). However, the recent identification of non-redox Tat substrates (such as, virulence factors from *Pseudomonas aeruginosa*) indicates a broader role for the pathway in bacterial protein secretion (Ochsner et al., *Proc. Natl. Acad. Sci. USA* 99:8312-8317 (2001); Voulhoux et al., *EMBO J.* 20:6735-6741 (2001); Dilks et al., *J. Bacteriol.* 185(4) (in press 2003)).

At least one copy of a TatA homolog and one copy of a TatC homolog are required for a functional Tat pathway (Bogsch et al., *J. Biol. Chem.* 273:18003-18006 (1998); Sargent et al., *EMBO J.* 17:3640-3650 (1998); Yen et al., 2002)). In certain prokaryotes (e.g., *E. coli*) and many other organisms, multiple copies of TatA have been found and may be involved in the translocation of different substrates, and an additional protein, TatB, has been found to be necessary for Tat-dependent secretion in *E. coli* (Sargent et al., *J. Biol. Chem.* 274: 36073-36082 (1999)). In *B. subtilis*, different TatC proteins are expressed under different conditions and seem to be responsible for the translocation of different substrates (Jongbloed et al., *J. Biol. Chem.* 275:41350-41357 (2000)).

The Tat pathway is distinct from the Sec pathway for, at least, the following reasons: (i) Tat substrates are secreted in a folded conformation (Hynds et al., *J. Biol. Chem.* 273: 34868-34874 (1998); Rodrigue et al., *J. Biol. Chem.* 274: 13223-13228 (1999); Thomas et al., *Mol. Microbiol.* 39:47-53 (2001)); (ii) Tat signal peptides contain a highly conserved twin arginine motif in their signal sequence (Cristobal et al., *EMBO J.* 18:2982-2990 (1999); Berks, *Mol. Microbiol.* 22:393-404 (1996) Berks et al., *Mol. Microbiol.* 35:260-274 (2000); Chaddock et al., *EMBO J.* 14:2715-2722 (1995); Niviere et al., *J. Gen. Microbiol.* 138 (Pt 10):2173-2183 (1992)); (iii) the energy necessary to drive translocation is provided solely by the proton motive force instead of ATP hydrolysis (Cline et al., *J. Biol. Chem.* 267:2688-2696 (1992); Santini et al., 1998)); and (iv) the Tat pathway is not a universally-conserved secretion mechanism (Wu et al., *J. Mol. Microbiol. Biotechnol.* 2:179-189 (2000); Yen et al., 2002)).

Because of its unique ability of secreting pre-folded protein substrate, the Tat pathway represents an alternative mechanism for the production of recombinant secreted proteins, particularly for those pre-folded in the cytoplasm of the bacteria. However, in most commonly used bacterial species, such as *E. coli*, or *B. subtilis*, the Tat secretion pathway is not as efficient as the Sec pathway, and is not suitable for secreting high level of recombinant proteins under normal physiological growth conditions.

Thus, there is a need to discover or design a more efficient Tat secretion pathway for heterologous protein production and secretion in a biotechnologically amenable organism. To this end, a means is needed for identifying putative Tat substrates. This is necessary to permit investigation of the correlation between the number of components of the Tat system and the number of putative Tat substrates, and to understand how stably and efficiently the folded protein substrate can cross the cytoplasmic membrane.

Microorganisms that naturally utilize the Tat pathway frequently are likely to use the pathway more efficiently. *Streptomyces* are gram-positive spore-forming soil microorganisms that are well know in the biotechnology for their production of a large variety of secondary metabolites, many of which have antimicrobial, antifungal, and immunosuppressive activities. While particularly noted for antibiotic production, certain strains of *Streptomyces* have served as hosts for the heterologous production of human proteins with therapeutic value. This is partly due to the availability of well-established plasmid-based expression systems, developed fermentation technology and a low level of endogenous protease activity (Engels and Koller, in Transgenesis—Application of Gene Transfer (Murray, ed.) Wiley & Sons, pp. 32-53 (1992)).

*Streptomyces* naturally produce many extracellular enzymes, and have the capacity to secrete large amounts of proteins. For example, *S. coelicolor* has been estimated to secrete as many as 800 proteins into the extra-cytoplasmic environment (Molnar, in Recombinant Microbes for Industrial and Agricultural Applications (Muruoka and Imanaka, eds) Markel Dekker, pp. 81-104 (1994); Gilbert et al., *Crit. Rev. Biotechnol.* 15:13-39 (1995)). Nevertheless, little is known about the mechanism of the Tat pathway in *Streptomyces*, let alone as attempt to use the Tat pathway for expressing heterologous proteins.

However, for every therapeutic protein that has been launched, hundreds more are in development. Many of these have been taken off the fast-track due to concerns about ways in which they can be manufactured efficiently, cheaply, and in large quantities. The secretion pathway currently utilized for mammalian cell culture and bacterial expression systems is limited to the production of proteins that fold correctly after translocation to the extra-cytoplasmic environment, but many proteins are incapable of folding correctly under those circumstances due to a lack of appropriate chaperones and other conditions, a fact which has held back the development of countless new treatments. Accordingly, a need has remained to exploit alternative methods to provide for the secretion of folded, active proteins in a highly specific and efficient manner that will be of critical importance to the pharmaceutical industry as it begins to investigate new therapeutic targets identified by the current advances in genomics.

SUMMARY OF THE INVENTION

The present invention studied the alternative twin arginine translocation (Tat) secretory pathway in *Streptomyces* and other bacterial species. It provides a means for evaluating and identifying putative substrates of the Tat secretory pathway. It also provides a simple way to produce and purify correctly folded heterologous proteins on a large scale using microorganisms, such as, *Streptomyces* as hosts and the Tat pathway therein. Thus, it still allows for protein purification from extra-cytoplasmic fractions.

Industrially tractable bacteria have been identified that are estimated to secrete more then 200 proteins via this alternative pathway. Moreover, it has been shown that these organisms efficiently secrete numerous heterologous proteins of interest in their correctly folded conformations by the use of selected signal leader sequences with a Tat motif to direct protein secretion through this alternative pathway. Thus, substrates that are of biotechnological interest are more likely to be efficiently secreted by microorganisms that naturally utilize the Tat pathway, such as *Streptomyces* strains, providing a mechanism for secretion of a larger number of fully-folded proteins, than through any of the other prokaryotic expression hosts, avoiding many of the problems encountered by the currently used Sec pathway.

It is an object of an embodiment of this invention, therefore, to provide methods for evaluating and identifying putative substrates utilizing a Tat secretory pathway, comprising comparing know and recorded amino acid sequences of a polypeptide in a microorganism against the Tat signal sequence motif, wherein the Tat signal sequence has the motif XRRXX within a first 35 N' terminal residues of the amino acid sequence of the polypeptide, wherein RR represents two adjacent arginine residues, and X designates positions restricted to other selected amino acid residues, as will be defined in greater detail below. It is a further object to provide those substrates that are identified by these methods.

It is a further object to produce recombinant proteins that are secreted via Tat secretion methods because in the extracellular environment there are fewer proteins, making it easier to isolate the protein of interest. By comparison, given the thousands of endogenous proteins inside of the host cell, separation of a protein of interest is very expensive and inefficient. However, the Sec pathway secretes unfolded proteins, and thus is unable to secrete a heterologously expressed protein that quickly folds in the cytoplasm, or one that has difficulty folding correctly in the external environment. Consequently, the ability of the Tat pathway to secrete folded proteins has made it the focus of the present invention.

Yet another object of the present invention is the production of desirable heterologous proteins from a *Streptomyces* bacterium utilizing the Tat pathway as a means of excretion. By fusing a selected signal sequence permitting optimal translocation efficiency to the N-terminus of the protein of interest, theoretically any protein of interest can be produced and secreted effectively. This is crucial in a market in which protein production is already important, and growing, as the pharmaceutical and biotech industries continue to develop new protein-based therapies, while struggling with facile, reliable and economical ways of producing proteins of interest.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures, which are not intended to be limiting.

FIG. 2A shows iodine vapor staining of *H. volcanii* expressing wild-type (AmyRR), or signal sequence-mutated (AmyKK) α-amylase, grown on rich medium supplemented with 0.2% soluble starch. Clear halos surrounding colonies indicate starch hydrolysis by extra-cytoplasmic α-amylase. FIG. 2B shows a western blot analysis of SDS-denatured cell extracts (cyt) and culture supernatants (sup) from *H. volcanii* expressing AmyRR or AmyKK.

DESCRIPTION OF PREFERRED EMBODIMENTS OF THE INVENTION

Figure 1:
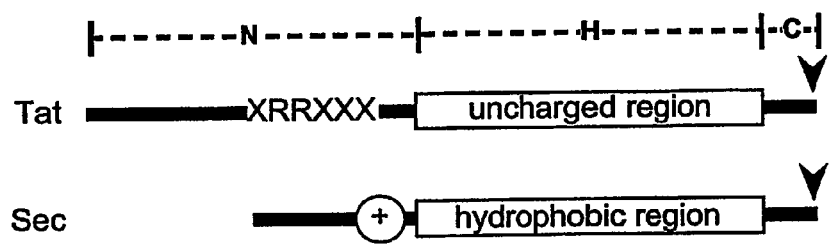
FIG. 1 diagrammatically shows how Tat signal sequences differ from those of the Sec system. Tat signal sequences are N-terminally extended, and typically have an XRRXXX (SEQ ID NO:1) motif within the first 35 residues, wherein X designates positions restricted to certain residues. Furthermore, an uncharged stretch following the RR motif is much less hydrophobic compared with the corresponding region in Sec signal sequences.

Protein-based therapies constitute a growing portion of pharmaceutical and biotechnology industries, and the cellular process of protein secretion has been heavily exploited to produce heterologous proteins on a large scale. When secreted into the cellular environment, the gene product can often be separated from the cells by simple filtration or centrifugation and will often be the predominant protein in the supernatant. Recombinant proteins are currently engineered so that they are secreted via the general secretion (Sec) pathway. However, the Sec pathway transports proteins in an unfolded state, and is thus useless for exporting a significant number of proteins that fold prematurely or are unable to fold correctly in a hostile extra-cytoplasmic environment.

In accordance with the present invention, a twin arginine translocation (Tat) pathway has been developed and utilized to permit the controlled secretion of large, fully-folded heterologous proteins. A folded protein is a protein that has acquired its tertiary structure. Only a correctly folded protein can carry out the intended activity or function of the protein.

The Tat pathway is a protein secretion pathway that translocates proteins across chloroplast and certain bacterial hydrophobic membranes via the Tat pore, which has the ability to transport large, folded proteins. The Tat machinery includes the cytoplasmic components, as well as the pore components in the membrane that target Tat substrates to the membrane and translocate the substrates across the membrane, respectively. Heterologously expressed proteins that fail to fold correctly in the extra-cytoplasmic environment due to the lack of chaperones, are more likely to be properly folded in the cytoplasmic environment, wherein a large number of chaperones are available to assist in the folding of the protein. Accordingly, translocation via the Tat pathway has a unique advantage that it allows for the secretion of proteins that are already folded, and thus allows for the simpler protein purification from extra-cytoplasmic fractions. Even proteins that fold too quickly in the cytoplasm can still be secreted into the external environment via the Tat pathway, permitting them to be efficiently purified.

Initially, the utilization of the Tat and Sec pathways were examined in *Halobacterium* sp. NRC-1 by analyzing the entire genome, as set forth in Example 1, below. To better understand the role played by the Tat pathway in protein translocation, in vivo analyses of halophilic (α-amylase provided experimental evidence for the utilization of the Tat pathway by the Halobacteriaceae. From this information, the inventors have determined that (i) nearly all known extracellular proteins of the Halobacteriaceae have typical Tat signal sequences; and (ii) homologs of these proteins in organisms other than Halobacteriaceae contain Sec signal sequences.

To identify putative Tat and Sec substrates from the *Halobacterium* sp. NRC-1 genome, a PERL program, TATFIND (later referred to as TATFIND 1.1, as modifications were made to the original program) was developed by the inventors (see, Rose et al., 2002) to distinguish between the structurally similar signal sequences of these two substrate types. Thus, a scan of entire *Halobacterium* sp. NRC-1 for Tat and Sec substrates confirmed that almost all secreted proteins from halophilic archaeon are putative Tat substrates. Therefore, it appeared that extensive use of the Tat pathway by the Halobacteriaceae represents an evolutionary solution to the problem posed by the need for stabilization of secreted proteins in high-salt conditions. Folding of the secreted haloarchael proteins before translocation (i) permit them to be stabilized, and (ii) prevent aggregation, both intracellularly and extracellularly. Moreover, chaperones, which can play a crucial role in correct folding of proteins, are present in the cytoplasm but absent from the supernatant fluids. Thus, folding prior to secretion benefits from the help of chaperones.

To identify putative Tat substrates in the *Halobacterium* sp. NRC-1 genome, a PERL program, TATFIND (later referred to as TATFIND 1.1, as modifications were made to the original program) was developed by the inventors (see, Rose et al., 2002. Thus, a scan of entire *Halobacterium* sp. NRC-1 for Tat and Sec substrates confirmed that almost all secreted proteins from halophilic archaeon are putative Tat substrates. Therefore, it appeared that the Halobacteriaceae extensively use of the Tat pathway, which likely represents an evolutionary solution to the problem posed by the need for stabilization of secreted proteins in high-salt conditions. Folding of the secreted haloarchael proteins before translocation (i) permit them to be stabilized, and (ii) prevent aggregation, both intracellularly and extracellularly. Moreover, chaperones, which can play a crucial role in correct folding of proteins, are present in the cytoplasm but absent from the supernatant fluids. Thus, folding prior to secretion benefits from the help of chaperones.

In accordance with the findings of the present invention, (i) nearly all homologs of putative non-redox Tat substrates from *Halobacterium* sp. NRC-1 were also predicted to be Tat substrates in other Halobacteriaceae; and (ii) the majority of putative *Halobacterium* sp. NRC-1 Tat substrates were non-redox proteins. In addition, TATFIND analysis of the nearly completed *H. volcanii* genome sequence demonstrated an extensive usage of the Tat pathway for secreted proteins, similar to that observed for *Halobacterium* sp. NRC-1.

While there are a number of computer programs, such as SIGNALP (Nielsen et al., *Protein Eng.* 10:1-6 (1997)) and PSORT, are designed to detect the signal sequences located on the N-terminus of Sec secreted proteins, they were developed before it was known that there was an alternative secretion mechanism. Consequently, such programs are unable to distinguish between Sec and Tat substrates, and thus are unable to predict the mechanism by which the protein is secreted (i.e., Sec or Tat).

TATFIND was designed by the inventors to detect essentially all of the properties of the signal sequence of the Tat secreted proteins TATFIND simplifies a tedious task, which until the present invention would have required the manual screening and comparison of all of the proteins in a genome. By comparison, TATFIND can search the entire *E. coli* genome for putative Tat substrates and yield output in less than 5 seconds. Moreover, it has proven to be highly accurate, despite the fact that putative structural determinants in the mature Tat substrate exist that have not yet been identified, and thus could not be included in TATFIND.

The algorithm as embodied in the present invention, when initially tested on the complete set of predicted proteins from the *Escherichia coli* genome, successfully identified all experimentally confirmed *E. coli* Tat substrates with double arginines, and made only 4 erroneous predictions. Moreover, when tested on an organism (*Methanococcus jannaschii*) known to not use the Tat pathway, since the Tat genes are themselves missing from the archaeon, the program identified no substrates. Thus, the criteria used by this program were shown to provide sufficient information to predict Tat substrates with a high level of reliability.

TATFIND reads a single text file (containing one or more amino acid sequences for a protein) in FASTA format, and searches them using a series of rules to determine if any of them are likely to be secreted via the Tat pathway. Putative candidates are printed out along with a hydrophobicity score for the a 13 hydrophobic amino acid stretch of the h-region following the twin arginine residues. To operate properly the FASTA formatted files preferably have at least 60 characters per line. A hash is set up based upon the hydrophobicity values taken from Cid et al., *Protein Eng.* 5:373-375 (1992), as follows: A=>0.02; R=>-0.42; N=>-0.77; D=>-1.04; C=>0.77; Q=>-1.10; E=>-1.14; G=>-0.80; H=>0.26; I=>1.81; L=>1.14; K=>-0.41; M=>1.00; F=>1.35; P=>-0.09; S=>-0.97; T=>-0.77; W=>1.71; Y=>1.11; V=>1.13. After grabbing the first 35 amino acids (aa) of each sequence, the program begins a series of tests "rules" for Tat discovery:

Rule #1 states: Can we find the Twin arginine motif in the first 35aa? If we can, locate and grab the 22aa upstream following the first arginine residue.

Therefore, there is established a pattern sought within those first 35 amino acids of the protein sequence, which is:

$$(X^{-1})R^0R^{+1}(X^{+2})(X^{+3})(X^{+4})$$ (Equation 1; SEQ ID NO:1)

wherein $X^{-1}$ is H, A, P, K, R, N, T, G, S, D, Q, or E; wherein $R^0R^{+1}$ represent the twin arginines, wherein $X^{+2}$ is A, P, K, R, N, T, G, S, D, Q, or E; wherein $X^{+3}$ is I, W, F, L, V, Y, M, C, H, A, P, N, or T (positively charged residues were excluded from this position); and wherein $X^{+4}$ is I, L, V, M, or F. The recognized single letter codes for amino acids are used consistently through this disclosure to represent the amino acids being identified as follows: alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), valine (V).

Rule #2 states: Is there a hydrophobic stretch of at least 13aa immediately following the "RR"? If so gather up information for rules #3a, #3b and #4.

Rule #3a states: Special case: TwinArg: single charges residue: hydrophobic region check for: RR [DERK] [hydrophobic stretch begins immediately] Tally up the hydrophobicity of the first 13 hydrophobic AA's. [Note that the term DERK instructs the program to look for amino acids aspartic acid (D) or glutamic acid (E) or arginine (R) or lysine (K). It does not refer to an amino acid sequence.]

Rule #3b states: Special case: RR [DERK] [hydrophobic region is here] Tally up the hydrophobicity of the first 13 hydrophobic residues.

Rule #4 states: If rule #3 doesn't apply, check for the presence of a basic residue immediately preceding the hydrophobic region. If not present, toss it out, otherwise we have we have a candidate. Tally up the hydrophobicity of the first 13 hydrophobic AAs.

If the pattern of Equation 1 was found, TATFIND assessed three additional criteria: (i) whether there was an uncharged stretch of at least 13 residues in the 22 residues following the R0; (ii) whether the uncharged stretch started behind a negatively charged residue (not allowed except behind positions +2 and +5) or behind a positively charged residue; and (iii) whether the hydrophobicity sum of the first 13 residues of the uncharged region was <8.0 according to Cid et al., 1992. If the above pattern was found and all the criteria were met, then a sequence was considered to be a putative Tat substrate.

Based upon the discovery that non-redox Tat substrates from *Halobacterium* sp. NRC-1 were also predicted Tat substrates in other Halobacteriaceae, the Tat process was evaluated 84 different microorganisms to determine the importance of this pathway in diverse bacteria and archaea (see Example 2). Using a genomic approach, and a slightly modified version of the TATFIND program (TATFIND 1.2), 84 diverse prokaryotic proteomes available from NCBI were evaluated, and from which a comprehensive list of putative Tat substrates was established.

TATFIND 1.2 still relies upon Equation 1 $((X^{-1})R^0R^{+1}(X^{+}2)(X^{+3})(X^{+4}))$, which remains SEQ ID NO:1, and the rules remained the same, as did the hydrophobicity values, but the residues permitted at each X value were expanded to include a possibility of M at position $X^{-1}$ and of Q at position $X^{+4}$. Therefore, TATFIND 1.2 applied the motif wherein $X^{-1}$ is M, H, A, P, K, R, N, T, G, S, D, Q, or E; wherein $R^0R^{+1}$ represent the twin arginines, wherein $X^{+2}$ is A, P, K, R, N, T, G, S, D, Q, or E; wherein $X^{+3}$ is I, W, F, L, V, Y, M, C, H, A, P, N, or T (positively charged residues were excluded from this position); and wherein $X^{+4}$ is Q, I, L, V, M, or F.

The results of the TATFIND studies, as well as phylogenetic analyses of Tat components, provided insight into the correlation between the number of components of the Tat system and the number of putative Tat substrates. Strikingly, these results indicated that contrary to earlier studies conducted by others on the bacterium *Escherichia coli*, the Tat pathway is utilized to highly varying extents. Many prokaryotes secrete a large number of proteins via the Tat pathway. Furthermore, while many prokaryotes use this pathway predominantly for the secretion of redox proteins, analyses of the predicted substrates indicated that certain bacteria and archaea secrete mainly non-redox proteins via the Tat pathway. While no correlation was observed between the number of Tat machinery components encoded by an organism and the number of predicted Tat substrates, it was noted that the composition of this machinery was specific to phylogenetic taxa.

The signal sequences of Tat substrates resemble those of Sec substrates, in that both contain a positively charged hydrophilic n-region, followed by a hydrophobic stretch (h-region) and, in most cases, a cleavage site (c-region) (FIG. 1). However, Tat signal sequences are often significantly longer than Sec signal sequences, due to an extension of the n-region, which contains the conserved twin arginine motif (RR) (two neighboring arginines). The h-region of Tat signal sequences has a less conserved amino acid pattern, and it is generally less hydrophobic than that of Sec signal sequences and often consists of an uncharged region with neutral hydrophobicity. TatA/tha4, TatB/hcf106, and TatC/cpTatC are the membrane components involved in Tat protein translocation in prokaryotes and chloroplasts, respectively.

In a preferred embodiment, the TATFIND-identified Tat signal sequence is used to effect the secretion of a large number of proteins into the surrounding environments via any of the prokaryotic expression hosts. However, as seen from the TATFIND analysis, most currently used Sec expression hosts have a low number of Tat substrates, and both the *B. subtilis* and the *E. coli* Tat systems are highly inefficient. Furthermore, it has been shown that only certain heterologously expressed proteins fused to an *E. coli* Tat signal sequence can be secreted, and that most of its native Tat substrates contain cofactors.

However, contrary to studies conducted in *E. coli*, many prokaryotes secrete a large number of proteins via the Tat pathway, most of which are non-redox proteins as reported by the inventors (see, Dilks et al., in press 2003). Thus, substrates that are of biotechnological interest are more likely to be efficiently secreted by *Streptomyces* strains, which appear to naturally use this pathway for a large number of proteins, in contrast to many other prokaryotic expression hosts. In fact, in accordance with the findings of the present invention, the industrially tractable organism *Streptomyces coelicolor*, well known for its production of numerous antibacterial agents, is predicted to secrete more than 200 diverse proteins using this pathway (Dilks et al., 2003). The genus *Streptomyces* belongs to the family Actinomycetes, which are high G+C organisms, of which many develop a mycelial habit. The *Actinomycete* genera are defined by partial sequence analysis of 16S ribosomal RNA. They are soil microorganisms that are well know in the biotechnology for their production of a large variety of secondary metabolites, many of which have antimicrobial, antifungal, and immunosuppressive activities.

While the Sec pathway has been exploited for heterologous protein production in *Streptomyces*, little attention has been given to the Tat pathway as a general secretion pathway for heterologously expressed proteins. *S. coelicolor* has one TatA and a TatC homolog and although a recent study (Schaerlaekens et al., *J. Bacteriol.* 183(23):6727-6732 (2001)) reported the characterization of a *S. lividans* TatC knockout, protein secretion analyses of the resulting mutant strain was only tested for its effect on translocation of two redox proteins, a bona fide *E. coli* Tat substrate and a *S. lividans* redox protein. However, it is the ability to secrete non-redox proteins via the Tat pathway that is of particular significance in the present invention, which has not previously been suggested. In accordance with the present invention, *Streptomyces* uses the Tat pathway as a general secretion pathway. In fact, prior to the discovery of the Tat pathway, researchers observed arginines in *Streptomyces* signal sequences ("Arg cluster") that, if deleted, abolished protein translocation.

Furthermore, although unaware of the Tat pathway at the time of publication, two independent research groups reported a significant increase in protein secretion when a Sec signal sequence was replaced with a signal sequence containing what has now been identified by the present invention as a typical Tat motif: 1) Chang et al. (in Biology of Actinomycetes '88, Proc. of Seventh Internat'l Symposium on Biology of Actinomycetes (Okami, Beppu and Ogawara, eds.), Japanese Sci. Soc. Press, Tokyo, p. 103 (1988)) taught fusing human TNF to the signal sequences of two *Streptomyces* proteins, MelF and Spt-II, wherein the former resulting in an 18-fold increase in secretion efficiency; and 2) Rowland et al. (*Applied Microbiol. Biotechnol.* 38(1):94-100 (1992)) replaced the *Flavobacterium* species phosphodiesterase signal sequence with the *S. coelicolor* galactosidase signal sequence, and observed an increased secretion efficiency of the thus heterologously expressed fusion protein in *S. lividans*. In hindsight, it now appears that both the MelF and β-galactosidase signal sequences contain typical Tat motifs presented in the present invention, confirming that 1) secretion of these constructs via the Tat pathway was more efficient than when the proteins were directed to the Sec pathway, and 2) identifying the *Streptomyces* Tat pathway as the most efficient route of secretion for heterologously expressed proteins.

In a preferred embodiment, however, using a *Streptomyces* strain, such as *S. coelicolor* or *S. lividans*, using the identified Tat signal sequence, establishes an ideal expression host for heterologously expressed proteins for at least the following reasons: 1) *Streptomyces* are non-pathogenic; 2) as previously noted, *Streptomyces* are Gram positive, meaning that they have no outer membrane as an additional barrier, and thus proteins are secreted directly into the supernatant; 3) the necessary genetic and biochemical tools are known in the art for *Streptomyces*, and available for heterologous expression (e.g., expression vectors, inducible promoters, protein purification protocols, etc); 4) well-established, large-scale fermentation protocols are available, e.g., Gilbert et al., *Crit. Rev. Biotechnol.* 15(1):13-39 (1995)); 5) efficient secretion of heterologous proteins fused to *S. coelicolor* Sec and Tat signal sequences has been demonstrated, albeit before the Tat pathway had been identified (Noack et al., *Gene* 68(1):53-62 (1988); Chang et al., 1988; Rowland et al., 1992; Bender et al., *Applied Microbiol. Biotechnol.* 34(2):203-207 (1990)); 6) *Streptomyces* contain a functional Tat pathway, as well as a large number of putative Tat substrates, indicating that these bacteria possess an efficient Tat pathway, and they contain a wide variety of Tat substrates, making them useful for the secretion of a diverse group of heterologous substrates; 7) moreover, regulatory agencies, such as the EPA and FDA, have an extensive history and are familiar with *Streptomyces*. Thus, the use of *Streptomyces* as expression host should not present additional difficulties for attaining regulatory approvals.

Heterologous proteins produced by recombinant techniques may be secreted and isolated from a mixture of cells or from medium containing the protein. "Recombinant DNA" is a molecule of containing DNA originating from two or more sources. The recombinant DNA encodes a recombinant protein, which may also be a "heterologous protein." A "heterologous protein" is a protein that is expressed in a host other than its native host (i.e., the organism that naturally contains the DNA encoding the protein). Methods for generating fusion constructs for effecting the controlled secretion of a heterologous protein from a microorganism are well known in the art, once the sequence of the desired gene is known (see, for example, Ausubel et al. (1993) Current Protocols in Molecular Biology, Greene and Wiley, New York), and in this case once the heterologous gene is under the control of a Tat signal sequence.

For secretion of the subject protein, a DNA sequence encoding an appropriate Tat signal peptide is linked to the 5' end of the nucleotide sequence encoding the protein, such that the signal peptide directs the linked composition to the Tat pore, resulting in secretion of the protein from the cell via the Tat pathway. A cell culture typically includes host cells, media and other byproducts. Suitable mediums for cell culture are well known in the art. Protein can be isolated from cell culture medium, host cells, or both using techniques known in the art for purifying proteins. Suitable prokaryotic combinations will be readily apparent to those of skill in the art and can be found, for example, *Molecular Cloning: A Laboratory Manual*, Cold Spring Harbor Laboratory, New York (1989); Hopwood, *Microbiology* 145(Pt 9):2183-2202 (1999)).

By "expression" is meant the process, after the DNA for the heterologous protein is delivered into the selected prokaryotic cell, by which a nucleotide sequence undergoes successful transcription and translation such that detectable levels of the delivered nucleotide sequence are expressed in an amount and over a time period that a measurable amount of the heterologous protein is produced within the cell, properly folded and secreted via the Tat pathway into the culture medium.

The language "nucleic acid molecule encoding a heterologous protein" is intended to include any nucleic acid molecule that will be transcribed and translated into said protein in its biologically active and fully folded form upon introduction of such nucleic acid molecule into a viable host cell (e.g., the molecule can further contain appropriate control elements comprising the Tat signal sequence for regulating expression in the cell). The nucleic acid molecule encoding the heterologous protein can consist of the coding region of the corresponding gene, or alternatively it can further contain noncoding regions, such as 5' or 3' untranslated regions, introns, fragments thereof, or other sequences.

A nucleic acid sequence (or gene) encoding a heterologous protein is isolated using any one of several known molecular procedures. For example, primers comprising conserved regions of the sequences of interest may be used as probes to isolate, by polymerase chain reaction (PCR) or by direct hybridization, as yet unknown homologs in a DNA library comprising specific DNAs. Alternatively, antibodies directed against such a protein may be used to isolate clones encoding the protein from an expression library comprising specific DNAs. The isolation of primers, probes, molecular cloning and the generation of antibodies are procedures that are well known in the art and are described, for example, by Sambrook et al. or Ausubel et al., supra, or by Harlow et al. (in Antibodies, A Laboratory Manual, Cold Spring Harbor, N.Y., 1988).

Thus, the invention also includes the resulting heterologous protein as expressed by the isolated nucleic acid sequence and secreted from the host cell via the Tat pathway, wherein the nucleic acid encodes a protein which has preferably, at least about 35% identity to the corresponding full-length native protein. More preferably, the secreted heterologous protein, or biologically active fragment thereof, has at least about 45%, more preferably, at least about 55%, yet more preferably, at least about 65%, even more preferably, at least about 75%, yet more preferably, at least about 85% identity, and more preferably having, at least about 95%, and even more preferably, at least about 99% identity to the corresponding full-length native protein see above.

Thus, the nucleic acid molecule intended for use in accordance with the present invention can encode the full-length heterologous protein or a peptide fragment thereof that is of sufficient length to be biologically active, i.e., having the biological characteristics of the naturally occurring protein or modified forms thereof. The invention is also intended to include the use of fragments, mutants, or variants (e.g., modified forms) of the inserted heterologous gene, so long as it is capable of encoding and expressing a biologically active form of the encoded protein of interest.

The terms "biologically active" or "biologically active form of the protein," as used herein, are meant to include forms of the heterologous protein that are capable of effecting the desired therapeutic activity of the native protein when used for its intended purposes. One skilled in the art can select such forms based upon the intended activity of the expressed and secreted protein via the Tat pathway. The activity of the resulting protein can be readily determined, for example, by comparing its functional ability with that of a comparable naturally occurring protein or one produced by standard means.

The nucleic acid used to encode the corresponding heterologous protein of interest can be a cDNA, or alternatively it can be a genomic DNA fragment. Mutants of the DNA sequence can be prepared and inserted into the host genome by a variety of known methods, such as, for example, by introducing nucleotide base pair modifications (e.g., substitutions, deletions, additions) to a nucleic acid molecule encoding the heterologous protein by standard methods, such as site-directed mutagenesis or polymerase chain reaction-mediated (PCR) mutagenesis.

Also included in the invention is a cell comprising an isolated nucleic acid encoding a heterologous protein secreted by the Tat pathway from the cell, and a cell comprising an isolated nucleic acid encoding a biologically active fragment thereof.

An "isolated" or "purified" protein or biologically active portion thereof is substantially free of cellular material or other contaminating proteins from the cell or tissue source from which the protein is produced and isolated, or substantially free of chemical precursors or other chemicals when the protein is chemically synthesized. Thus, protein that is substantially free of cellular material includes preparations of protein having less than about 30%, 20%, 10%, or 5% (by dry weight) of contaminating proteins. When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest.

An isolated biologically active polypeptide can have several different physical forms. The isolated heterologous polypeptide can exist as a full-length nascent or unprocessed polypeptide, or as partially processed polypeptides or combinations of processed polypeptides. The full-length nascent polypeptide can be postranslationally modified by specific proteolytic cleavage events that results in the formation of fragments of the full-length nascent polypeptide. A fragment, or physical association of fragments can have the biological activity associated with the full-length polypeptide, however, the degree of biological activity associated with individual fragments can vary. Accordingly, the present invention also provides for analogs of the heterologous proteins or peptides encoded by the isolated nucleic acid sequences introduced into the host cells for expression via the Tat pathway.

Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Mutant forms of the protein of interest that have amino acid substitutions, deletions and/or additions as compared to the naturally occurring amino acid sequence of a comparable native protein molecule, yet still retain the functional activity of the natural form of protein as described herein are also encompassed by the invention. To retain the functional properties, preferably only conservative amino acid substitutions are made at one or more amino acid residues.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Modifications (which do not normally alter primary sequence) include in vivo, or in vitro chemical derivatization of the subject polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation. Also embraced are sequences having phosphorylated amino acid residues, e.g., phosphotyrosine, phosphoserine, or phosphothreonine.

Also included are polypeptides that have been modified using ordinary molecular biological techniques so as to improve their resistance to proteolytic degradation or to optimize solubility properties or to render them more suitable as a therapeutic agent. Analogs of such polypeptides include those containing residues other than naturally-occurring L-amino acids, e.g., D-amino acids or non-naturally occurring synthetic amino acids. However, the peptides of the invention are not limited to products of any of the specific exemplary processes listed herein.

To express a heterologous protein as encoded by a nucleic acid molecule from a host cell, the nucleic acid must be operably linked to regulatory elements. "Operably linked" is intended to mean that the nucleotide sequence encoding the expressed protein is linked to at least one regulatory sequence in a manner which allows expression of the nucleotide sequence and secretion from the cell via the Tat pathway. Regulatory sequences are selected to direct expression of the desired protein in an appropriate host cell. Accordingly, the term "regulatory sequence" includes promoters, enhancers and other expression control elements. Such regulatory sequences are known to those skilled in the art and are further described, for example, in Goeddel, *Gene Expression Technology: Methods in Enzymology* 185, Academic Press, San Diego, Calif. (1990).

These regulatory elements include those required for transcription and translation of the nucleic acid encoding the protein(s), and may include, in addition to the Tat signal sequence of the present invention, promoters, enhancers, polyadenylation signals, and sequences necessary for transport of the molecule to the appropriate cellular compartment to permit secretion from the cell via the Tat pore. When the nucleic acid is a cDNA in a recombinant expression vector, the regulatory functions responsible for transcription and/or translation of the cDNA are often provided by viral sequences. Examples of commonly used viral promoters include those derived from polyoma, adenovirus 2, cytomegalovirus and simian virus 40, and retroviral LTRs. However, the promoter activity may be endogenously provided by the host cell.

Regulatory sequences linked to the cDNA can be selected to provide constitutive or inducible transcription. Inducible transcription can be accomplished by, for example, use of an inducible enhancer. Thus, in a specific embodiment of the invention the nucleic acid molecule encoding the heterologous fusion protein is under the control of an inducible control element, such that expression of the protein can be turned 'on' or 'off' (or intermediate levels in between) using an agent which affects the inducible control element (e.g., expression can be modulated by modulating the concentration of the inducing agent in the cell). This allows for switching 'on' or 'off' of the expression of the subject protein in the host cell, or the systems necessary for the enhanced proliferation of the host cells.

When the nucleic acid molecule encoding a heterologous protein is operably linked to regulatory elements, it is typically carried in a vector. A "vector" is a composition of matter which comprises nucleic acids, and which can be used to effect the secretion of the heterologous protein from the cell via the Tat mechanism, under the direction of the identified Tat signal sequence. The vector carries the gene encoding the fusion protein and a promoter that allows for the expression of the protein, whereas the Tat machinery allows for secretion. Numerous vectors are known in the art including, but not limited to, linear polynucleotides, polynucleotides associated with ionic or amphiphilic compounds, plasmids, viruses or other nucleic acid molecules comprising, for example, sequences that are necessary for selection and amplification of the nucleic acid molecule in bacteria. Thus, the term vector includes an autonomously replicating plasmid or a virus.

The term should also be construed to include non-plasmid and non-viral compounds, which facilitate transfer of nucleic acid into cells, such as, for example, polylysine compounds, liposomes, and the like. "expression vector" refers to a vector comprising a recombinant polynucleotide comprising expression control sequences operatively linked to the nucleotide sequence encoding the heterologous protein to be expressed from the host cell. Thus, a nucleic acid molecule comprising a nucleotide sequence or gene encoding the heterologous protein operably linked to regulatory control elements, is also referred to herein as an "expression vector." An expression vector comprises sufficient cis-acting elements for expression; whereas other elements for expression can be supplied by the host cell or an in vitro expression system.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or be introduced into the same cell by co-transfection. Additional elements may also be needed for optimal synthesis of protein mRNA. These elements may include splice signals, as well as transcription promoters, enhancers, and termination signals. cDNA expression vectors incorporating such elements include those described by Okayama et al., *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferably, vectors can be replicated in *E. coli* (for easy cloning) and then be transferred into *Streptomyces* where they also can replicate because they have two origins of replication (i.e., shuttle vectors). Alternatively, 'integration vectors,' are used which can replicate in *E. coli* (for easy cloning) and integrate into the *Streptomyces* chromosome by homologous recombination.

Expression vectors include all those known in the art, such as cosmids, plasmids (e.g., naked or contained in liposomes) and viruses that incorporate the recombinant polynucleotide. Expression vectors within the scope of the invention, therefore, comprise a nucleic acid encoding the subject heterologous protein as described herein and a promoter operably linked to the nucleic acid, further comprising the Tat signal sequence to control the secretion of the expression product in fully folded form from the cell via the Tat pathway. Such expression vectors can be used to transfect host cells to thereby produce the protein encoded by the nucleic acid as described herein. An expression vector of the invention, as described herein, typically further includes nucleotide sequences encoding the heterologous protein operably linked to at least one "regulatory sequence."

An expression vector of the invention can be used to transfect cells, either prokaryotic or eukaryotic (e.g., mammalian, insect or yeast cells), but preferably prokaryotic, and more preferably *Streptomyces*, to thereby produce proteins encoded by nucleotide sequences transported by the vector. Expression in prokaryotes is most often carried out with vectors containing constitutive or inducible promoters. Certain expression vectors (so called fusion-vectors) are designed to add a number of amino acid residues to the expressed recombinant protein, usually to the amino terminus of the expressed protein. These are well known in the art and commercially available. One strategy to maximize expression of a heterologous protein in accordance with the present invention, is to express the protein from a host bacterium which has an impaired capacity to proteolytically cleave the protein of interest within or outside the cell, particularly when the protein is a recombinant protein.

As regulatory sequences have been described above, it should be understood that the design of the expression vector may depend on such factors as the choice of the host cell to be transfected, and/or the type and/or amount of protein desired to be expressed.

A "host-vector system" refers to host cells, which have been transfected with appropriate vectors using recombinant DNA techniques. The vectors and methods disclosed herein are suitable for use in host cells over a wide range of prokaryotic organisms when the DNA is operatively linked to a promoter that is highly active in the selected prokaryotic cells. The preferred host vector system is one utilizing the Tat expression pathway for secreting proteins into the extra-cytoplasmic environment, more preferably one in which the host has been entirely characterized and sequenced, even more preferably a *Streptomyces*, or *Pseudomonas* or even an *E. coli*.

Most preferably the hosts are of the *Streptomyces* family of microorganisms, of which the *S. lividans* or *S. coelicolor* are very useful, or in the alternative, the hosts may be other microorganisms, wherein expression and secretion is controlled by the *Streptomyces* signal sequences and the secretion kinetics are those of the *Streptomyces* Tat substrates.

The nucleic acid molecule encoding a heterologous protein can be introduced into the host cell by various methods typically referred to as transfection. The terms "tansfection" or "transfected with" refers to the introduction of exogenous nucleic acid into a host cell and are intended to encompass a variety of techniques useful for introduction of nucleic acids into such cells, including electroporation, calcium-phosphate precipitation, DEAE-dextran treatment, lipofection, microinjection, and viral infection. In particular, inserting DNA into *Streptomyces* requires making protoplasts or conjugation, for example, such methods are described in Kieser, et al., *Practical Streptomyces Genetics* (Norwich; John Innes Foundation) p. 613 (2000). Suitable methods for transfection can be found in Sambrook et al. (*Molecular Cloning: A Laboratory Manual*, $2^{nd}$ Ed., Cold Spring Harbor Laboratory Press (1989)) and other laboratory textbooks.

A number of procedures may be used to assess whether the microorganism comprises the desired heterologous nucleic acid, and whether the protein of interest has been secreted. For example, genomic DNA obtained from the cells of the transgenic microorganism may be analyzed by Southern blot hybridization or by PCR to determine the length and orientation of any inserted transgenic nucleic acid present therein. Northern blot hybridization analysis or PCR may be used to characterize mRNA transcribed in cells of the transgenic microorganism. The procedures for performing such analyses are well known in the art and are described, for example, in Sambrook et al., a western blot analysis may be used to identify, characterize or quantify any expressed proteins or polypeptides that are secreted into the culture medium, using e.g., antibody raised against the selected heterologous protein or active fragments thereof. In situations where a heterologous polypeptide is expressed in a catalytically active form, PC biosynthesis assays may be used to identify and characterize the enzyme molecules so expressed.

The Tat pathway, like the Sec pathway, has proven to be a general secretion apparatus, potentially allowing for the translocation of a wide variety of heterologous substrates. Thus, in a preferred embodiment, the fusion of a *Streptomycete* Tat signal sequence (i.e., one having the identified Tat motif) to a biologically valuable protein allows for the efficient production of the active protein targeted to the Tat machinery, thereby permitting translocation of the protein in a fully-folded manner. A signal sequence of the Tat pathway is a sequence of amino acids at the N-terminus of a Tat substrate that has a specific structure and sequence motif that is recognized by the Tat machinery. Tat substrates are proteins that contain a Tat signal sequence, and in turn, are targeted to and translocated across the hydrophobic membrane via the Tat machinery.

Moreover, several of the putative Tat substrates in prokaryotes themselves are likely to be useful for biotechnological uses when provided with an expression host with an effective Tat translocation system. Furthermore, the absence of Tat translocon components (TatA/B and TatC) in mammals, along with the observation that the elimination of a functional TatC attenuates virulence of *P. aeruginosa*, suggest that the Tat translocon may represent a novel antibiotic target (Ochsner et al., 2002; Voulhoux et al., 2001).

The present invention is further described by example. Nevertheless, the following examples are not to be construed as limiting the scope of the appended claims.

EXAMPLES

The following experiments were conducted to evaluate the Tat secretory process in a necessarily diverse set of microorganisms to provide direct evidence of the importance of this pathway in bacteria and archaea, and to develop program means for identifying putative Tat substrates among the set of all putative coding sequences (CDS) from entire genomes.

Example 1

TATFIND 1.1

To examine utilization of the Tat and Sec pathways in Haloobacteriaceae, analyses were conducted in *Haloobacterium* sp. NRC-1, currently the only known complete genomic sequence of a halophilic archaeon. The entire genome was analyzed using the following strategy: (i) a Tat substrate recognition program (TATFIND) was developed to detect putative Tat substrates in *Halobacterium* sp. NRC-1 (this program, described in greater detail below, is based on the position and sequence of the Tat pattern, as well as on the position, length and hydrophobicity of an uncharged region following the twin-arginine pattern); (ii) usage of the Sec pathway in *Halobacterium* sp. NRC-1 was examined by identifying putative secreted proteins with SIGNALP (Nielsen et al., 1997); (iii) all SIGNALP-positive candidates were analyzed further with the TMHMM program (Sonnhammer et al., *Proc. Int. Conf. Intell. Syst. Mol Biol.* 6:175-182 (1998)) that predicts membrane spanning segments, thereby eliminating proteins with multiple membrane-spanning segments; and (iv) all remaining candidates were classified based on their subcellular localization. Because in any genome analysis, only a fraction of coding sequences (CDS) can be positively identified, the proteins chosen for analysis were encoded by annotated CDS and it was assumed that such subsets were representative of the whole population of CDS. A detailed map of the analyses and complete results of individual steps of the process can be accessed on the Internet at sas.upenn.edu/~pohlschr (herein incorporated by reference in the entirety).

Sequences Used in the Analyses

All predicted proteins (identified and putative) as annotated in GenBank records [NC_000917.1 (*Archaeoglobus fulgi-dus*); AE004437, AE004438 (plasmid NRC100) and NC_001869.1 (plasmid NRC200) (*Halobacterium* sp. NRC-1)] were analyzed to identify putative Tat and Sec substrates. Furthermore, U00096.1 (*Escherichia coli* K12); NC_000909, NC_001732 (large extra-chromosomal element), NC_001733 (small extra-chromosomal element) (*Methanococcus jannaschii*); NC_000854.1 (*Aeropyrum pernix* K1); and AE006641 (*Sulfolobus solfataricus*)] were analyzed to identify putative Tat substrates.

Tat Substrate Prediction

A PERL program (TATFIND) was written to identify putative Tat substrates among the set of all putative coding sequences (CDS) from the entire genome. The patterns recognized by TATFIND were taken from the list of putative secreted proteins from *Halobacterium* sp. NRC-1, and then refined with residues found in putative Tat substrates from other Halobacteriaceae. The position of the pattern in the N-terminus, as well as the length and position of the following uncharged region, was adjusted according to known extrema in bacterial Tat substrates (i.e., *Zyniomonas mobilis* glucose: fructose oxidoreductase (GFOR): largest n-region with RR at position 30/31; *E. coli* HybO: shortest uncharged stretch of only 13 residues length; *E. coli* NapG: uncharged stretch begins nine residues behind the RR motif) (Halbig et al., 1999; Robinson et al., 2001; Stanley et al., 2001).

The version TATFIND, used to analyze the complete set of predicted proteins of all species described in this work, searched for the following pattern between residues 2 and 35 of the predicted protein: $(X^{-1})R^0R^{+1}(X^{+2})(X^{+3})(X^{+4})$, where the amino acid at position $X^{-1}$ had a hydrophobicity score (0.26; $X^{+2}$ had a hydrophobicity score (0.02; $X^{+3}$ had a hydrophobicity score (–0.77 (positively charged residues were excluded from this position); and $X^{+4}$ was one of the following residues (I, L, V, M, or F). All hydrophobicity values were taken from Cid et al., 1992). If the above pattern was found, TATFIND assessed three additional criteria: (i) whether there was an uncharged stretch of at least 13 residues in the 22 residues following the RR; (ii) whether the uncharged stretch started behind a negatively charged residue (not allowed except behind positions +2 and +5); and (iii) whether the hydrophobicity sum of the first 13 residues of the uncharged region was <8.0. If the above pattern was found and all the criteria were met, then a sequence was considered to be a putative Tat substrate.

Identification and Analysis of Putative Tat Substrates

Applying TATFIND to the *Halobacterium* sp. NRC-1 genome, 64 putative secreted Tat substrates were identified. Of these, 34 had detectable homologs with assigned functions that could be classified into one of four groups: (i) eight putative extracellular enzymes; (ii) 13 binding proteins; (iii) seven redox proteins; and (iv) six other surface proteins (See, Rose et al., 2002, herein incorporated by reference). Homologs of putative *Halobacterium* sp. NRC-1 Tat substrates were identified in other organisms by BLASTP and screened with TATFIND and SIGNALP to determine whether they were potential Tat or Sec substrates respectively. Although all haloarchaeal homologs were putative Tat substrates, the non-haloarchaeal homologs of all non-redox Tat substrates were putative Sec substrates (Table 1).

Identification of Putative Tat Substrates in Non-Halobacteriaceae

The same analyses were carried out with three additional non-halophilic archaeal genomes. Only eight putative Tat substrates were identified in *Archaeoglobus fulgidus*, a thermophilic non-halophilic euryarchaeon closely related to *Halobacterium* sp. NRC-1 (Table 1). Consistent with previous findings, of the seven proteins that had assigned functions, six were putative redox proteins. Similarly, in two thermophilic crenarchaeota, *Sulfolobus solfataricus* and *Aeropyrum pernix*, only four and 10 putative Tat substrates, respectively, were identified. Of these, all the assigned substrates were putative redox proteins (Table 1).

TABLE 1

Classification of putative archaeal Tat substrates.

| | Halobacterium sp. NRC-1 | Archaeoglobus fulgidus | Sulfolobus solfataricus | Aeropyrum pernix |
|---|---|---|---|---|
| Redox proteins | 7 | 6 | 3 | 2 |
| Redox proteins | 7 | 6 | 3 | 2 |
| Non-redox proteins | 27 | 1 | 0 | 0 |
| Non-redox proteins | 27 | 1 | 0 | 0 |

The accuracy of TATFIND was assessed by screening the genomes of (i) *Escherichia coli*, which has been estimated to contain more than 400 exported proteins including 26 that are known or hypothesized to be secreted via the Tat pathway; and (ii) *Methanococcus jannaschii*, which lacks homologs of the Tat translocation genes. TATFIND predicted 34 substrates in *E. coli*, successfully identifying all 26 previously reported Tat substrates (Robinson et al., 2001; Stanley et al., 2001). Most remarkably, this algorithm did not predict any proteins in *M. jannaschii*, which is consistent with the lack of the Tat genes in this methanogen. In addition, TATFIND identified no cytoplasmic proteins in *A. fulgidus, A. pernix* and *S. solfataricus*.

Taken together, these results supported the previous findings that the extensive use of the Tat pathway is an unusual feature of protein secretion in the Halobacteriaceae, and confirmed that TATFIND is a suitable tool for the prediction of Tat substrates in a broad range of prokaryotes.

Identification of Putative Archaeal Sec Substrates

To determine the significance of the relatively high number of putative extracellular Tat substrates identified in the Halobacteriaceae, it was necessary to examine the utilization of the Sec pathway for haloarchaeal secretion. This required multiple steps. SIGNALP (Nielsen et al., 1997) was used to identify putative signal sequence-containing proteins from the complete set of all predicted proteins. However, since SIGNALP has not been trained specifically to recognize archaeal signal sequences, broad parameters were used and options for Gram negative, Gram positive, and eukaryotic signal sequence predictions were included, as well as a lenient cut-off value (3 'yes' responses by at least one predictive option). Of the SIGNALP positives, all TATFIND-positive proteins were excluded. From this subset, proteins with TMHMM-predicted transmembrane helices (Sonnhammer et al., 1998) outside the N-terminal 50 residues were removed, as these proteins are not secreted, but rather, are integral membrane proteins.

Putative Sec substrates from *Halobacterium* sp. NRC-1 were identified by submitting all CDS to SIGNALP. However, SIGNALP predictions cannot be considered to be Sec pathway specific per se, as this program is not able to clearly distinguish between substrates of the Sec and Tat translocation pathways, because the overall structure of Tat and Sec signal sequences is conserved. Furthermore, the Sec machinery, unlike the Tat pathway, does not recognize specific amino acid patterns. Therefore, TATFIND was used to identify and eliminate putative Tat substrates from the SIGNALP output.

All putative proteins that were positive by TATFIND or SIGNALP (after removing integral membrane proteins) were analyzed further by BLASTP to identify homologs (E-value $(10^{10})$ (Altschul et al., *J. Mol. Biol.* 215:403-410 (1990)). The homologs were then examined, and cytoplasmic proteins were removed. The non-cytoplasmic homologs were then analyzed by TATFIND, SIGNALP and TMHMM to determine their potential mode of secretion.

Of the SIGNALP positives, 171 did not contain membrane-spanning segments past the first 50 amino acids, as identified by TMHMM. Fifty of these could be putatively identified by BLASTP analysis, of which the majority (33) were false positives as they had significant similarity to cytoplasmic or membrane proteins. Furthermore, five proteins had significant similarity to flagellins, which are known to use a specialized translocation system. The remaining 12 proteins were putative Sec substrates, although their cell surface localization was evident in only three cases, including a homolog of a type IV protease and two proteins involved in uptake pathways. In contrast, when similar analyses were conducted with the *A. fulgidus* genome, it was observed that the majority of proteins were secreted via the Sec pathway. These results indicated that the vast majority of putative secreted proteins of *Halobacterium* sp. NRC-1 are translocated via the Tat pathway.

Functional Analysis of the Haloarchaeal Tat Motif In Vivo

It is known that the exchange of the twin arginines (RR) with lysines (KK) in the twin-arginine motif of Tat substrates results in a block of Tat-dependent protein translocation in *E. coli* (Stanley et al., 2001). Thus, to determine the Tat specificity of an extracellular halophilic protein, the RR of the (α-amylase precursor from the alkalihalophile *Natronococcus* sp. strain Ah36 (Kobayashi et al., *J. Bacteriol.* 176:5131-5134 (1994)) (AmyRR) was replaced with KK (AmyKK).

Construction of Wild-Type and Signal Sequence Mutant α-Amylase

Plasmids. The twin-arginine residues of the wild-type *Natronococcus* sp. strain Ah-36 (Kobayashi et al., 1994) α-amylase signal sequence were replaced with twin-lysine residues using site-directed polymerase chain reaction (PCR) mutagenesis. A 125 bp fragment encompassing the 5' end of the α-amylase gene (including 57 bp upstream of the open reading frame, ORF) was PCR amplified (forward primer 5'-GTTAGCACTAAGCTTCGAAACCGAA TTAAAAT-CATTAT-3' (SEQ ID NO:2); reverse primer 5'-CGAGCG-CAGGACGGTCTTTTT GTCGATACCCGCCG-3' (SEQ ID NO:3)) from pANAM121 (which harbors the wild-type α-amylase; Kobayashi et al., 1994), thus replacing the twin arginines at amino acid positions 16 and 17 with twin lysines. A second 1543 bp fragment encompassing the α-amylase ORF starting from nucleotide 91 (amino acid 11) was PCR amplified (forward primer 5'-TCGGCGGGTATCGA-CAAAAAGACCGTCC TGCGCTCG-3' (SEQ ID NO:4); reverse primer 5'-GACTGT GGTACCTCAGTCGTCGTCG-GACAG-3' (SEQ ID NO:5)) from pANAM121.

These two fragments were ligated together using a modified PCR, and the product was PCR amplified (forward primer 5'-GTTAGCACTAAGCTTCGAAACCGAAT-TAAAATCATT AT-3' (SEQ ID NO:6); reverse primer 5'-GACTGTGGTACCTCAGTCGTCGTCGGA CAG-3' (SEQ ID NO:7)) to produce the final signal sequence mutant α-amylase insert (AmyKK). The wild-type α-amylase insert (AmyRR) was also generated by PCR using these two primers. Both inserts were cut with HindIII and KpnI and cloned into pMLH3 (Holmes et al., *Gene* 146: 117-121 (1994)), resulting in the expression vectors pAMY-KK and pAMY-RR. These constructs were then used to transform *H. volcanii* (strain WFD11) (Charlebois et al., *Proc. Natl. Acad. Sci. USA* 84: 8530-8534 (1987); Cline et al., *J. Bacteriol.* 171:4987-4991 (1989)).

Expression and Detection of Wild-Type and Signal Sequence Mutant α-Amylase

Figure 2:
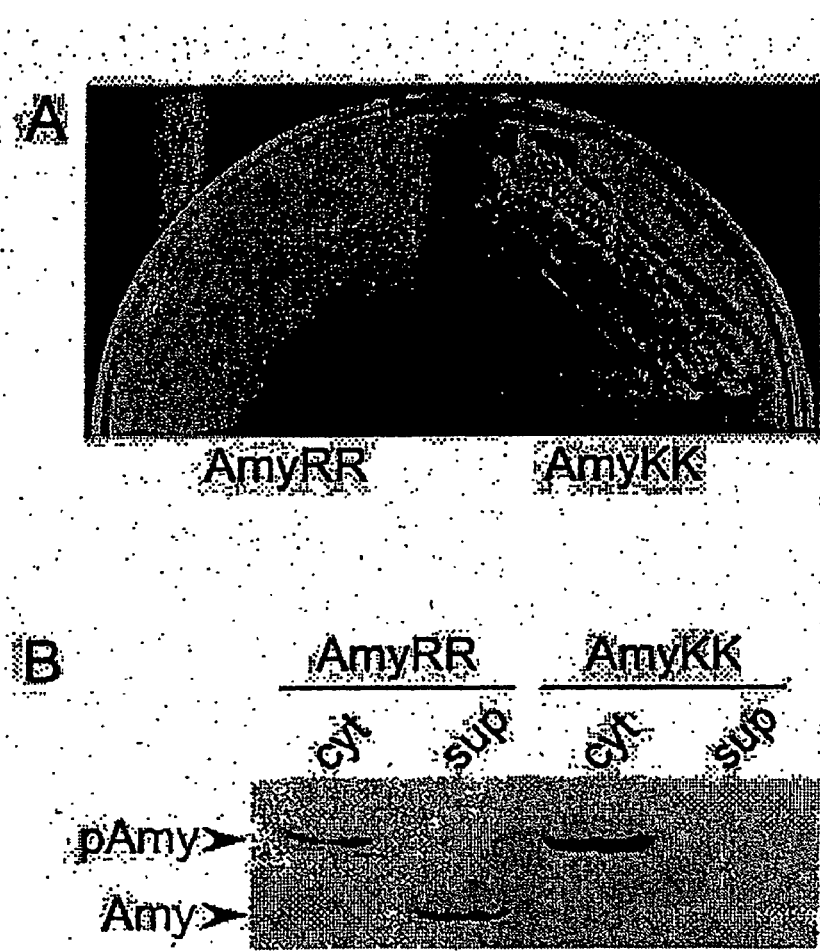
FIGS. 2A and 2B photographically show that the secretion of halophilic α-amylase requires the twin-arginine Tat motif.

In vivo starch hydrolysis assay. Secretion of the wild-type and mutant α-amylase was examined by a starch hydrolysis assay. Both *H. volcanii* harboring signal sequence-mutated pAMY-KK and *H. volcanii* expressing wild-type pAMY-RR were grown on rich medium (Charlebois et al., 1987) supplemented with 0.2% soluble starch. Once single, separated colonies were visible, the plates were exposed to iodine vapor to detect starch hydrolysis by extra-cytoplasmic α-amylase. Clear halos surrounding a colony indicated starch hydrolysis by extra-cytoplasmic α-amylase (FIG. 2A).

Immunoblot analysis. To confirm that α-amylase was synthesized in these cells, Western blot analysis of SDS-denatured cell extracts (cyt) and culture supernatants (sup) from *H. volcanii* expressing either AmyRR or AmyKK was performed (FIG. 2B). Cells were cultured in rich medium to an absorbance (600 nm) of 0.6, pelleted and lysed with SDS-PAGE sample buffer. The cell supernatant was precipitated with 10% trichloroacetic acid. Samples were electrophoresed on a SDS-polyacrylamide gel, electroblotted to nitrocellulose, probed with a polyclonal antibody against α-amylase and visualized with the ECL chemiluminescent system (Amersham).

It was observed that the export of active AmyKK was blocked. This was indicated by the absence of clear halos around cells grown on starch medium that was exposed to iodine vapor (FIG. 2A). Immunoblot analysis of culture supernatants and cell extracts confirmed that the enzyme was synthesized in both cell types, but was secreted only in cells harboring wild-type α-amylase (FIG. 2B). Approximately 90% of α-amylase activity was present in the culture supernatant of wild-type cells, whereas only cell-associated activity was observed for cells expressing AmyKK (data not shown), indicating that this halophilic α-amylase can fold inside the cytoplasm, and that the twin-arginine motif is indeed essential for its secretion.

Example 2

TATFIND 1.2 and TATFIND 1.3

A refined TATFIND program was used to look at all prokaryotic genomes available at NCBI. The recent identification of novel Tat substrates in *P. aeruginosa* (Ochsner et al., 2002) permitted the extension of the rules of TATFIND 1.1 to allow a methionine at position $X^{-1}$, and glutamine at position $X^{+4}$, thus creating a second program, TATFIND 1.2. Mutational analyses of certain Tat signal sequences suggested that in specific instances the substitution of lysine, asparagine, and glutamine for one of the two conserved arginines does not prevent Tat-dependent export However, only two naturally occurring Tat substrates are known to deviate from the conserved 'RR' motif in their signal sequence. Therefore, modifications of the program allowing for a variable RR motif due to these recent reports were not included in the present study, as these were likely to be exceptions that would lead to strong overprediction.

Tat Substrates—TATFIND 1.2 and TATFIND 1.3

TATFIND 1.2 predicted that the Tat pathway is utilized to varying extents in the various organisms that were analyzed, based on the number and identity of their putative Tat substrates (Table 2). TATFIND 1.2 identified all previously-confirmed Tat substrates containing twin arginine motifs in *E. coli* and other prokaryotes (Jongbloed et al., 2000; Ochsner et al., 2002; Robinson et al., *Nat. Rev. Mol. Cell Biol.* 2:350-356 (2001); Stanley et al., *J. Bacteriol.* 183:139-144 (2001); Voulhoux et al., 2001) and predicted few or no substrates of this pathway in organisms which lack all Tat component homologs or contained only a TatA homolog (e.g., *Chlamydia trachomatis* and *Methanopyrus kandleri* AV19, respectively) (Table 2). Strikingly, in the analyses of the 29 prokaryotic genomes with zero or one identified Tat component(s), only 37 false positives were predicted (including cytoplasmic, membrane and secreted proteins), of which only 4 were putative secreted Sec substrates. Thus, the program is highly efficient in distinguishing Tat signal peptides from Sec signal peptides.

TABLE 2

Predicted Tat Substrate and Component Numbers in a Diverse Group of Prokaryotes.

| Organism | Domain | Phylum | ORFs | # of TATFIND 1.2 Positives | Tat Components A/E | B | C |
|---|---|---|---|---|---|---|---|
| *Streptomyces coelicolor* A3(2) | bac | Actinobacteria | 7899 | 145 | 1 | | 1 |
| *Mesorhizobium loti* | bac | Proteobacteria (alpha) | 7279 | 95 | 1 | — | 1 |
| *Sinorhizobium meliloti* | bac | Proteobacteria (alpha) | 6206 | 94 | 1 | 1 | 1 |
| *Caulobacter crescentus* | bac | Proteobacteria (alpha) | 3737 | 88 | 1 | 1 | 1 |
| *Ralstonia solanacearum* | bac | Proteobacteria (beta) | 5116 | 71 | 1 | 1 | 1 |
| *Halobacterium* sp. NRC-1 | archaea | Euryarchaeota | 2446 | 68 | 1 | — | 2 |
| *Pseudomonas aeruginosa* | bac | Proteobacteria (gamma) | 5567 | 57 | 1 | 1 | 1 |
| *Xanthomonas campestris* 3391 | bac | Proteobacteria (gamma) | 4181 | 55 | 1 | 1 | 1 |
| *Agrobacterium tumefaciens* | bac | Proteobacteria (alpha) | 5299 | 51 | 1 | 1 | 1 |
| *Xanthomonas axonopodis* 306 | bac | Proteobacteria (gamma) | 4312 | 50 | 1 | 1 | 1 |
| *Escherichia coli* K12 | bac | Proteobacteria (gamma) | 4279 | 34 | 2 | 1 | 1 |
| *Escherichia coli* O157-H7 EDL933 | bac | Proteobacteria (gamma) | 5335 | 33 | 2 | 1 | 1 |
| *Salmonella typhimurium* LT2 | bac | Proteobacteria (gamma) | 4559 | 33 | 2 | 1 | 1 |
| *Escherichia coli* O157-H7 | bac | Proteobacteria (gamma) | 5361 | 32 | 2 | 1 | 1 |
| *Mycobacterium tuberculosis* H37Rv | bac | Actinobacteria | 3927 | 31 | 1 | — | 1 |
| *Nostoc* sp. PCC7120 | bac | Cyanobacteria | 6129 | 31 | 2 | — | 1 |
| *Mycobacterium tuberculosis* CDC1551 | bac | Actinobacteria | 4187 | 29 | 1 | — | 1 |
| *Salmonella enterica* Typhi | bac | Proteobacteria (gamma) | 4768 | 28 | 2 | 1 | 1 |
| *Deinococcus radiodurans* | bac | Deinococcus-Thermus | 2997 | 22 | 2 | — | 1 |

TABLE 2-continued

Predicted Tat Substrate and Component Numbers in a Diverse Group of Prokaryotes.

| Organism | Domain | Phylum | ORFs | # of TATFIND 1.2 Positives | Tat Components A/E | B | C |
|---|---|---|---|---|---|---|---|
| Synechocystis sp. PPC6803 | bac | Cyanobacteria | 3167 | 21 | 2 | — | 1 |
| Yersinia pestis | bac | Proteobacteria (gamma) | 4083 | 19 | 2 | 1 | 1 |
| Brucella melitensis | bac | Proteobacteria (alpha) | 3199 | 19 | 1 | — | 1 |
| Xylella fastidiosa 9a5c | bac | Proteobacteria (gamma) | 2768 | 17 | 1 | 1 | 1 |
| Aquifex aeolicus | bac | Aquificae | 1529 | 15 | 2 | — | 1 |
| Corynebacterium glutamicum | bac | Actinobacteria | 3041 | 15 | 2 | — | 1 |
| Pyrobaculum aerophilum | archaea | Euryarchaeota | 2605 | 14 | 1 | — | 1 |
| Neisseria meningitidis Z2491 | bac | Proteobacteria (beta) | 2065 | 12 | 1 | 1 | 1 |
| Pasteurella multocida | bac | Proteobacteria (gamma) | 2015 | 12 | 1 | 1 | 1 |
| Campylobacter jejuni | bac | Proteobacteria (epsilon) | 1654 | 11 | 1 | 1 | 1 |
| Neisseria meningitidis MC58 | bac | Proteobacteria (beta) | 2079 | 11 | 1 | 1 | 1 |
| Haemophilus influenza | bac | Proteobacteria (gamma) | 1714 | 9 | 1 | 1 | 1 |
| Archaeoglobus fulgidus | archaea | Euryarchaeota | 2420 | 9 | 2 | — | 2 |
| Mycobacterium leprae | bac | Actinobacteria | 2720 | 9 | 1 | — | 1 |
| Vibrio cholerae | bac | Proteobacteria (gamma) | 3835 | 7 | 2 | 1 | 1 |
| Bacillus subtilis | bac | Firmicutes | 4112 | 7 | 3 | — | 2 |
| Aeropyrum pernix | archaea | Crenarchaeota | 1840 | 7 | 2 | — | 1 |
| Methanosarcina mazei Goe1 | archaea | Euryarchaeota | 3371 | 6 | 2 | — | 2 |
| Treponema pallidum | bac | Spirochaetes | 1036 | 6 | — | — | — |
| Bacillus halodurans | bac | Firmicutes | 4066 | 5 | 2 | — | 2 |
| Methanosarcina acetivorans str.C2A | archaea | Euryarchaeota | 4540 | 5 | 2 | — | 2 |
| Sulfolobus solfataricus | archaea | Crenarchaeota | 2977 | 5 | 3 | — | 2 |
| Chlorobium tepidum TLS | bac | Chlorobi | 2252 | 5 | 2 | — | 1 |
| Pyrococcus horikoshii | archaea | Euryarchaeota | 1801 | 5 | — | — | — |
| Sulfolobus tokodaii | archaea | Crenarchaeota | 2826 | 4 | 2 | — | 1 |
| Helicobacter pylorii 26695 | bac | Proteobacteria (epsilon) | 1576 | 3 | 1 | 1 | 1 |
| Helicobacter pylorii J99 | bac | Proteobacteria (epsilon) | 1491 | 3 | 1 | 1 | 1 |
| Clostridium perfringens | bac | Firmicutes | 2723 | 3 | — | — | — |
| Pyrococcus furiosus DSM3638 | archaea | Euryarchaeota | 2065 | 3 | — | — | — |
| Thermotoga maritima | bac | Thermotogae | 1858 | 3 | — | — | — |
| Listeria innocua | bac | Firmicutes | 3043 | 2 | 1 | — | 1 |
| Staphylococcus aureus Mu50 | bac | Firmicutes | 2714 | 2 | 1 | — | 1 |
| Staphylococcus aureus MW2 | bac | Firmicutes | 2632 | 2 | 1 | — | 1 |
| Staphylococcus aureus N315 | bac | Firmicutes | 2625 | 2 | 1 | — | 1 |
| Thermoplasma acidphilum | archaea | Euryarchaeota | 1482 | 2 | 1 | — | 1 |
| Thermoplasma volcanium | archaea | Euryarchaeota | 1500 | 2 | 1 | — | 1 |
| Chlamydia trachomatis | bac | Chlamydiae | 895 | 2 | — | — | — |
| Chlamydophila pneumoniae AR39 | bac | Chlamydiae | 1112 | 2 | — | — | — |
| Chlamydophila pneumoniae CWL029 | bac | Chlamydiae | 1054 | 2 | — | — | — |
| Pyrococcus abyssi | archaea | Euryarchaeota | 1769 | 2 | — | — | — |
| Listeria monocytogenes EGD-e | bac | Firmicutes | 2846 | 1 | 1 | — | 1 |
| Rickettsia conoril | bac | Proteobacteria (alpha) | 1374 | 1 | 1 | — | 1 |
| Rickettsia prowazekii | bac | Proteobacteria (alpha) | 835 | 1 | 1 | — | 1 |
| Chlamydia muridarum | bac | Chlamydiae | 909 | 1 | — | — | — |

TABLE 2-continued

Predicted Tat Substrate and Component Numbers in a Diverse Group of Prokaryotes.

| Organism | Domain | Phylum | ORFs | # of TATFIND 1.2 Positives | Tat Components A/E | B | C |
|---|---|---|---|---|---|---|---|
| *Chlamydophila pneumoniae* J138 | bac | *Chlamydiae* | 1069 | 1 | — | — | — |
| *Clostridium acetobutylicum* | bac | *Firmicutes* | 3848 | 1 | — | — | — |
| *Lactococcus lactis* subsp. *lactis* | bac | *Firmicutes* | 2267 | 1 | — | — | — |
| *Methanothermo-bacter thermauto-trophicus* | archaea | *Euryarchaeota* | 1873 | 1 | — | — | — |
| *Streptococcus pneumoniae* R6 | bac | *Firmicutes* | 2043 | 1 | — | — | — |
| *Streptococcus pyogenes* | bac | *Firmicutes* | 1697 | 1 | — | — | — |
| *Streptococcus pyogenes* MGAS8232 | bac | *Firmicutes* | 1845 | 1 | — | — | — |
| *Thermoanaerobacter tengcongensis* | archaea | *Euryarchaeota* | 2588 | 1 | — | — | — |
| *Buchnera aphidicola* | bac | *Proteobacteria* (gamma) | 545 | — | — | — | — |
| *Buchnera* sp. APS | bac | *Proteobacteria* (gamma) | 564 | — | — | — | — |
| *Fusobacterium nucleatum* 25586 | bac | *Fusobacteria* | 2067 | — | — | — | — |
| *Methanococcus janaschii* | archaea | *Euryarchaeota* | 1729 | — | — | — | — |
| *Methanopyrus kandleri* AV19 | archaea | *Euryarchaeota* | 1687 | — | 1 | — | — |
| *Mycoplasma genitalium* | bac | *Firmicutes* | 484 | — | — | — | — |
| *Mycoplasma pneumoniae* | bac | *Firmicutes* | 689 | — | — | — | — |
| *Mycoplasma pulmonis* | bac | *Firmicutes* | 782 | — | — | — | — |
| *Streptococcus pneumoniae* TIGR4 | bac | *Firmicutes* | 2094 | — | — | — | — |
| *Ureaplasma urealyticum* | bac | *Firmicutes* | 614 | — | — | — | — |
| *Borrelia burgdorferi* | bac | *Spirochaetes* | 1638 | — | — | — | — |

Some organisms (e.g., *Rickettsia prowazekii* and *Staphylococcus aureus*) seem to have maintained the Tat pathway for the secretion of a small number of proteins. In fact, TATFIND 1.2 identified only one Tat substrate for *R. prowazekii* and two for *S. aureus* (Table 2). By comparison, other bacteria and archaea appear to make extensive use of this pathway, which originally was thought to be required for the translocation of only a minor subset of secreted proteins (Table 1). For example, 88, 94, and 145 putative Tat substrates were identified in *Caulobacter crescentus, Sinorhizobium meliloti*, and *Streptomyces coelicolor*, respectively (Table 2). While analyses of putative Sec substrates suggest that the haloarchaea remain the only organisms that use this pathway for the translocation of the majority of their secreted proteins, the present findings indicate that some prokaryotes use the Tat pathway for the secretion of as many as 20% of their extra-cytoplasmic proteins (see also, Bentley et al., *Nature* 417:141-147 (2002)).

The diverse utilization of the Tat pathway observed in the 84 prokaryotes was also observed within phylogenetically-related groups. For example, a range of 9 (*Mycobacterium leprae*) to 145 (*S. coelicolor*) putative Tat substrates were identified in the bacterial phylum Actinobacteria (Table 2). Similarly, the number of predicted Tat substrates were observed to vary widely within the phyla Proteobacteria, Cyanobacteria, Euryarchaeota, and Crenarchaeota (Table 2). Consequently, the degree to which the Tat pathway is used is apparently quite variable, even among related organisms.

To further characterize the utilization of the Tat pathway by the prokaryotes examined in this study, the function and localization of TATFIND 1.2 positive proteins of 4 organisms were identified by their annotation (or that of their homologs) in the SWISS-PROT database. Since the Tat pathway has been shown to play a role only in the transport of secreted proteins, known and putative multi-spanning membrane proteins (as predicted by TMHMM (Sonnhammer et al., 1998) and cytoplasmic proteins were excluded from further analyses. Proteins that were predicted to be secreted in *Pyrobaculum aerophilum* were exclusively redox proteins, while the majority of putative Tat substrates of the gram-positive *Bacillus subtilis*, the gram-negative *C. crescentus* and the archaeon *Halobacterium* sp. NRC-1 were found to be non-redox proteins (Table 3). A relatively large number of the TATFIND 1.2 positive non-redox proteins found in *C. crescentus* and *Halobacterium* sp. NRC-1 were identified as substrate-binding proteins, a phenomenon also predicted for the plant pathogen *Agrobacterium tumefaciens*. Thus, while some organisms seem to preferentially use this pathway for the secretion of redox proteins (similar to *E. coli*, see Table 3), the Tat pathway is responsible for the secretion of a wider variety of substrates in other organisms.

TABLE 3

Classification of TATFIND 1.2 positives

| Organism | Secreted Redox | Secreted Non-redox | Cytoplasmic/ Integral Membrane | # annotated function or localization |
|---|---|---|---|---|
| B. subtilis | 1 | 2 | 0 | 4 |
| P. aerophilum | 7 | 0 | 0 | 7 |
| E. coli K-12 | 12 | 5 | 6 | 11 |
| Halobacterium sp. NRC-1 | 5 | 17 | 1 | 45 |
| C. crescentus | 6 | 28 | 5 | 49 |

For comparative purposes, only proteins whose function and putative localization could be determined (see text) were classified into redox, non-redox, and cytoplasmic/integral membrane.

Certain protein homologs were identified as Tat substrates in many prokaryotes. Analyses of some redox proteins, such as the dimethyl sulfoxide reductase chain A (DmsA), found in many of the 84 organisms analyzed, revealed that the majority of the DmsA homologs in these prokaryotes contained Tat signal peptides (see supplemental webpage CD) where all proteins identified by TATFIND from all 84 genomes are listed on the webpage]. More surprisingly, however, virtually all homologs of certain non-redox proteins, such as alkaline phosphatase D and phospholipase C, were found to have typical Tat signal sequences (see, Dilks et al., 2003). As a result, there may exist an unknown selective pressure favoring the conserved targeting of these and other non-redox proteins to the Tat pathway.

An exception to the observed Tat motif conservation among phospholipase C homologs was found in *Xanthomonas axonopodis*. One of its two phospholipase C homologs was found to contain an aspartic acid residue at position $X^{+2}$ (a variation not accepted by the rules of TATFIND 1.2). While this phospholipase C homolog may in fact not be a Tat substrate, this single deviation may also reflect the existence of certain organism-specific Tat substrate characteristics. Possible organism specificity is also indicated by the 54 additional putative Tat substrates identified in *S. coelicolor* when alanine is allowed at position $X^{+4}$ as suggested by Ochsner et al., 2002. Alanine at this position, however, does not markedly affect predictions for virtually all other organisms (data not shown), although additional versions of TATFIND may be developed that are tailored to phylogenetically related groups of organisms.

Thus, identification of *S. coelicolor* and other prokaryotic Tat substrates are most accurately achieved by using TATFIND 1.3, which differs from TATFIND 1.2 as it allows alanine at position $X^{+4}$. The additional putative Tat substrates identified by TATFIND 1.3 in *S. coelicolor* are listed below in Table 4, showing in a single representative species the additional sequences that can be identified simply by permitting alanine at position $X^{+4}$. TATFIND 1.3 continues to rely upon Equation 1 $((X^{-1})R^0 R^{+1}(X^{+2})(X^{+3})(X^{+4}))$, which remains SEQ ID NO:1, and the rules remained the same, as do the hydrophobicity values, but the residues permitted at each X value were expanded to include a possibility of A at position $X^{+4}$. Therefore, TATFIND 1.3 applies the motif wherein $X^{-1}$ is M, H, A, P, K, R, N, T, G, S, D, Q, or E; wherein $R^0 R^{+1}$ represent the twin arginines, wherein $X^{+2}$ is A, P, K, R, N, T, G, S, D, Q, or E; wherein $X^{+3}$ is I, W, F, L, V, Y, M, C, H, A, P, N, or T (positively charged residues were excluded from this position); and wherein $X^{+4}$ is A, Q, I, L, V, M, or F. The possibility of harboring an alanine at this position of the Tat signal sequence has also been suggested by preliminary in vivo analyses of a *Pseudomonas aeroginosa* Tat substrate.

TABLE 4

Additional TATFIND 1.3 positives in *S. coelicolor* 3(2) putative Tat substrates that were not found using TATFIND 1-2

| Gi number | Reference | Putative function or localization |
|---|---|---|
| 21225458 | NP_631237.1 | Putative secreted amidase |
| 21224914 | NP_630693.1 | Putative secreted protein |
| 21224715 | NP_630494.1 | Putative gamma-glutamyltranspeptidase (putative secreted protein) |
| 21224693 | NP_630472.1 | Putative lipoprotein |
| 21224487 | NP_630266.1 | Putative secreted protein |
| 21224144 | NP_629923.1 | Putative aminotransferase |
| 21223819 | NP_629598.1 | Putative secreted protein |
| 21223806 | NP_629585.1 | Putative ABC transporter |
| 21223805 | NP_629584.1 | Putative neutral zinc metalloprotease |
| 21223787 | NP_629566.1 | Putative integral membrane transport protein |
| 21223681 | NP_629460.1 | Polyketide beta-ketoacyl synthase alpha |
| 21223627 | NP_629406.1 | Secreted protein |
| 21223309 | NP_629088.1 | Putative integral membrane protein |
| 21222967 | NP_628746.1 | Putative membrane protein |
| 21222748 | NP_628527.1 | Putative integral membrane protein |
| 21222646 | NP_628425.1 | Putative secreted protein |
| 21222540 | NP_628319.1 | Phosphate-binding protein precursor |
| 21222270 | NP_628049.1 | Putative membrane protein |
| 21222223 | NP_628002.1 | Putative membrane protein |
| 21222221 | NP_628000.1 | Putative D-alanyl-D-alanine carboxypeptidase |
| 21221844 | NP_627623.1 | Putative ABC transporter transmembrane component |
| 21221843 | NP_627622.1 | Putative glutamate decarboxylase |
| 21221454 | NP_627233.1 | Putative lipoprotein |
| 21221288 | NP_627067.1 | Putative secreted endoglucanase |
| 21221278 | NP_627057.1 | Probable amino acid ABC transporter protein, solute-binding component |
| 21221218 | NP_626997.1 | Putative secreted ribonuclease |
| 21221214 | NP_626993.1 | Putative secreted protein |
| 21221169 | NP_626948.1 | Putative secreted protein |
| 21221157 | NP_626936.1 | Putative secreted protein |
| 21220742 | NP_626521.1 | FecCD-family membrane transport protein |
| 21220739 | NP_626518.1 | Putative membrane protein |
| 21220703 | NP_626482.1 | Putative maltose-binding protein |
| 21220616 | NP_626395.1 | Putative integral membrane protein |
| 21220523 | NP_626302.1 | Putative membrane protein |
| 21220426 | NP_626205.1 | Putative secreted protein |
| 21220393 | NP_626172.1 | Putative secreted protein |
| 21220369 | NP_626148.1 | Putative secreted protein |
| 2122313 | NP_626092.1 | Secreted subtilisin-like protease |
| 21220235 | NP_626014.1 | Putative secreted serine protease |
| 21220228 | NP_626007.1 | Putative secreted cellulose-binding protein |
| 21220103 | NP_625882.1 | Putative membrane protein |
| 2122007 | NP_625850.1 | Putative oxidoreductase |
| 21219820 | NP_625599.1 | Putative integral membrane protein |
| 21219739 | NP_625518.1 | Putative secreted tripeptidylaminopeptidase |
| 21219565 | NP_625344.1 | Putative secreted oxidoreductase |
| 21219513 | NP_625292.1 | Putative lipoprotein |
| 21219470 | NP_625249.1 | Putative solute-binding protein |
| 21219086 | NP_624865.1 | Putative histidine kinase protein |
| 21219051 | NP_624830.1 | Putative lipoprotein |
| 21219035 | NP_624814.1 | Putative iron-siderophore permease transmembrane protein |
| 21219021 | NP_624800.1 | Putative secreted protein |
| 21219020 | NP_624799.1 | Putative secreted chitin binding protein |
| 21234268 | NP_639879.1 | Putative secreted protein |

Tat Components in Sequenced Prokaryotes

Expanding on previous analyses by others of the Tat pathway, the presence of TatA, TatB and TatC was evaluated in all organisms analyzed using PSI-BLAST and its iterations (Table 2 and Altschul et al., *Nucleic Acids Res.* 25:3389-3402 (1997)). Detailed phylogenetic analyses revealed that all bacteria in the obligate intracellular pathogen phylum Chlamydiae completely lacked Tat components. Conversely, the presence of the Tat machinery was conserved in all crenarchaeota, actinobacteria, cyanobacteria, and proteobacteria (with the exception of the obligate symbiotic genus *Buchnera*) that were examined, even though the extent to which this machinery was utilized varied dramatically within each phylum (Table 2). Interestingly, homologs of TatB, found exclusively in the proteobacteria, were missing from only a few organisms in the α-subdivision (Table 2).

In the archaeal phylum euryarchaeota and the bacterial phylum firmicutes, approximately half of the organisms analyzed had components of the Tat machinery. However, a number of organisms from these phyla, unlike the proteobacteria or actinobacteria, were found to contain multiple copies of TatC (Table 2; Yen et al., 2002). It is intriguing that the majority of the firmicutes and euryarchaeota were predicted to have a relatively small number of putative Tat substrates, which suggests that in prokaryotes there is no direct correlation between the number of Tat substrates and TatC homologs. Furthermore, an additional examination of the 84 proteomes demonstrated that the number of TatA homologs or the presence of a TatB homolog in any of these organisms is also unrelated to the number of Tat substrates. This notion was underscored by the observation that *B. subtilis* contains three TatA and two TatC homologs, yet has only seven putative Tat substrates (Table 2).

Example 3

Cloning of *Streptomyces* Tat Components and Putative Tat Substrates

To determine the role and efficiency of a *Streptomyces*, the preferred organism was *S. lividans* because as an expression host include 1) it does not secrete a blue pigment like *S. coelicolor*, and 2) it does not require non-methylated DNA. However, the genome for *S. lividans* has not yet been completely sequenced. Therefore, *S. coelicolor*, was selected for the following analysis because it is highly homologous to *S. lividans*, its genome has been fully sequenced, permitting a TATFIND analysis of the genome, and complete characterization of the genomic information for the strain was advantageous for the analysis. It is intended that the findings in *S. coelicolor* are also applicable to the closely related *S. lividans*, as well as to other *Streptomyces* strains.

Accordingly in vivo analyses were initiated of the Tat pathway in *S. coelicolor*. A His-tagged version of the *S. coelicolor* Tat C components were cloned into a *Streptomyces* integration vector and expressed in its wild-type, *S. coelicolor* native host. An integration vector is one that when transformed into *Streptomyces* will recombine onto the chromosome at a specific site. Consequently there is not an independent plasmid in the cytoplasm, which could otherwise become problematic. In addition, upstream and downstream parts of the *S. coelicolor* TatC were cloned and an apramycin resistance gene was inserted between these regions into a conjugative plasmid, wherein DNA is transferred directly from one bacterium (*E. coli*) to another—*S. coelicolor*. This construct is used for the construction of a TatC knockout (see Schaerlaekens, 2001). Methods for conjugation and recombination are described, for example, in the Kieser manual.

Identification of the Role of the Tat Pathway in *Streptomyces*

Computational analyses of the *S. coelicolor* genome revealed that a large number of secreted proteins contain a typical Tat signal sequence. Therefore, in vivo analyses are conducted to complement the TATFIND results and to define *Streptomyces* specific Tat signal sequences.

*S. coelicolor* TatC Knockout

*S. lividans* has recently been shown to contain a functional Tat pathway, since a TatC knockout failed to secrete two redox proteins, the *E. coli* TorA, (a bona fide Tat substrate) as well as the *S. lividans* nitrate reductase, a redox protein with a typical Tat signal sequence. Because the TATFIND analyses suggested that *Streptomyces* also secrete a large number of non-redox proteins via this pathway, to identify, in vivo, substrates that depend on the Tat pathway, (Dilks et al., in press 2003) a comparison is undertaken to compare secreted proteins from an *S. coelicolor* TatC knockout strain, with those of a wild-type *S. coelicolor*. This permits extensive proteomic analyses of the estimated more than 200 putative *S. coelicolor* Tat substrates.

The *S. coelicolor* knockout is constructed in a fashion similar to that used for the construction of the *S. lividans* TatC. Briefly, a plasmid containing approximately 800 bp of tatC flanking regions interrupted by an apramycin resistance gene that have been cloned into an *E. coli* vector containing a second *Streptomyces* resistance gene (spectinomycin) is transformed into *S. coelicolor*. Apramycin resistant colonies that do not confer resistance to spectinomycin are screened by replica-plating to identify cells in which the tatC has been interrupted.

Identification of Putative *S. coelicolor* Tat Substrates

Although it is believed that *Streptomyces* uses the Tat pathway extensively, it has been demonstrated that the *S. lividans*, TatC is not essential for growth on rich medium. Given the close relationship between *S. lividans* and *S. coelicolor*, it is therefore concluded that the *S. coelicolor* Tat pathway is also not essential and that both strains are viable when grown in rich medium. After growing the strains to mid or late log phase or stationary phase supernatant fractions of *S. coelicolor* wild-type (wt) and tatC knockout strains are collected, and two dimensional (2D) gel electrophoresis is performed on the concentrated extracellular fraction. Proteins bands present in gels containing supernatant fractions from *S. coelicolor* (wt) strains, but that are absent or present in significantly lower concentrations in the gels containing the supernatant fractions of the mutant knockout strains, are putative Tat substrates that failed to be secreted via the Tat pathway. Matrix-Assisted Laser Desorption/Ionization Mass Spectrometry (MALDI-MS) is used to identify the masses of each tryptic fragment (the cleavage product of a proteins that has been treated with a protease) and will be compared to the calculated masses of tryptic fragments of all *S. coelicolor* proteins.

This is a preferred method for identifying proteins from sequenced genomes, since it is rapid and, more importantly, requires significantly lower amounts of the pure protein than other methods (e.g., N-terminal sequencing). However, in cases in which post-translational modifications would prevent this method of detection, purified proteins obtained in co-purification experiments can also be submitted for internal sequencing, mass spectroscopy (MS) analysis or LC-MS-MS (e.g., Quadrupole Time-Of-Flight (Q-TOF) MS), which can produce partial amino acid sequence data from silver-stained proteins. The resulting partial amino acid sequences are compared with the *S. coelicolor* genome database or the National Center for Bioinformatics (NCBI) databases to determine their sequence homology with previously-characterized *Streptomyces* proteins.

Once identified, the genes are cloned into shuttle vectors that can replicate in both *S. coelicolor* and *E. coli*. The genes are expressed from either their own promoters or from a *Streptomyces* promoter already cloned into the shuttle vectors. This approach not only permits verification of TATFIND predicted Tat substrates, but it is intended to also identify additional S. coelicolor Tat substrates. For example, as mentioned above, it is likely that permitting an additional "A" in position $X^{+4}$ in Equation 1 of the TATFIND program, will add an additional 50 Tat substrates to the S. coelicolor list, making them available for identification by this in vivo approach.

Signal sequences of proteins that were identified by TAT-FIND, but which could not be identified by the approach described above are then analyzed. The protein is expressed with a histidine (His)- or Flag-tag in the wild-type and mutant strains, and the secretion pattern observed. If both strains secrete the protein with similar efficiencies, it is likely that this motif, while a Tat motif in other organisms, is not recognized by the S. coelicolor Tat pathway. A control Sec substrate is included to exclude the possibility that a S. coelicolor Tat mutant is indirectly affecting Sec translocation.

These analyses permit the identification of a large number of bona fide Tat substrates in S. coelicolor and provide more definitive information concerning a typical S. coelicolor Tat signal sequence. Similarly, these steps can be applied to other species and strains of prokaryotes to determine the Tat substrates, if available.

Secretion Kinetics of Expressed Homologous and Heterologous Proteins Via the *Streptomyces* Tat Pathway Determination of the translocation efficiency of S. coelicolor Tat substrates. Protein translocation of Tat substrates across the E. coli cytoplasmic membrane via the Tat pathway is very inefficient. However, this Gram negative bacterium secretes only a minor subset of its secretome via this pathway, and most of the proteins are cofactor-containing proteins. In contrast, the present data suggest that S. coelicolor secretes more than 200 proteins of various classes via this pathway. It is thus likely that *Streptomyces* has optimized its Tat translocation system for the efficient secretion of a diverse group of substrates.

To determine the translocation efficiency of Tat substrates using the S. coelicolor Tat pathway, a number of S. coelicolor substrates are selected, including (i) different classes of proteins (binding-protein, redox-protein, hydrolases), and (ii) proteins with various Tat signal sequences that contain distinct amino acid compositions, varying lengths of the signal sequence, and/or varying lengths of the uncharged region. The proteins are fused with a C-terminal tag (e.g., 6×His, Flag, myc), and cloned into a *Streptomyces* intergration or expression vector (pIJ101 derivatives, such as pBM6) under the control of their own or heterologous *Streptomyces* promoters, e.g., like the inducible tip promoter. Pulse-chase experiments are conducted to determine the kinetics of protein secretion. These analyses are intended to indicate the efficiency of protein translocation across the S. coelicolor cytoplasmic membrane, and potentially indicate preferred signal peptide sequences.

Highly efficient production of heterologous proteins fused to a Sec signal sequence in *Streptomyces* has previously been reported Chang et al. (in Biology of Actinomycetes '88, Proc. of Seventh Internat'l Symposium on Biology of Actinomycetes (Okami, Beppu and Ogawara, eds.), Japanese Sci. Soc. Press, Tokyo, p. 103 (1988)), Rowland et al. (*Applied Microbiol. Biotechnol.* 38(1):94-100 (1992)). However, this will only work for proteins that fold after secretion, and that will fold correctly in the extracellular environment. Therefore, the identified S. coelicolor signal sequences are fused to a protein of biotechnological interest (heterologous protein, e.g., TNF, interferon gamma) intended to be secreted in a folded conformation via the Tat translocation pathway. As mentioned above, increased production of TNF fused to a putative *Streptomyces* Tat signal sequence compared to a Sec signal sequence in S. lividans has been reported, albeit without any knowledge that the effect was a result of the Tat pathway (Chang et al., 1988). While the mature part of the protein might be a crucial determinant for efficiency of translocation, signal sequences are chosen for proteins that have been shown to be secreted efficiently (see above).

If western blot analyses of cell and supernatant fractions indicate efficient secretion of the fusion construct, the kinetics of protein translocation is determined using pulse-chase analyses as described above. Activity assays specific for the expressed proteins are carried out to determine whether the proteins were correctly folded in the S. coelicolor cytoplasmic fraction. Also the efficiency of signal sequence targeting is tested to determine substrate specificity. Finally, because S. coelicolor has not been used extensively for the production of heterologous proteins, the expression of the fusion proteins are compared in other Streptomycetes, like S. lividans, to determine a good expression host.

Tat Signal Sequence Mutagenesis

While the analyses of various signal sequences for their efficiency of protein translocation provides general characteristics of signal sequences and information regarding secretion efficiency, this approach is not effective for screening for identifying the most efficient signal sequences, although it definitely provides the foundation for further analyses of the *Streptomyces* Tat translocation system. Thus, screens are further developed to permit mutagenisis of the Tat signal sequences and to identify the most effective ones for targeting heterologous proteins to and translocating across the cytoplasmic membrane of *Streptomycetes*. For this purpose, a screen is employed that is similar to that used to identify the more efficient of the Tat signal sequences in E. coli.

Briefly, in E. coli, mutagenized *Streptomyces* Tat signal sequences are fused to a green fluorescent protein (GFP), that in turn is fused to a cytoplasmic protease recognition site. Fusion proteins that are secreted into the periplasm are stable, whereas proteins retained in the cytoplasm are degraded. The fluorescence intensity of *Streptomyces* cells is determined by flow cytometry. Because *Streptomyces* are Gram positive, they do not have a periplasm. Therefore, secreted proteins are released into the external environment. The preferred screen does not require a protease site on the GFP, rather the fluorescence is monitored. Accordingly, a decrease in fluorescence indicates more efficient secretion of the fusion protein into the external environment, permitting optimization of the secretion of fully-folded heterologous proteins by the Tat pathway. To eliminate signal sequence mutations that result in decreased protein production, pulse-chase analyses with signal sequence mutant constructs are used to determine secretion kinetics.

Thus, the present invention provides a method for identifying signal sequences that efficiently target heterologous proteins to the *Streptomyces* Tat translocon, and to extensively characterize the Tat machinery in order to achieve high yields of active heterologous proteins allowing for their economic production.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

The invention claimed is:

1. A method for evaluating and identifying putative substrates utilizing a Tat secretory pathway, comprising:
   a) reading a text file containing one or more amino acid sequences for a predicted protein;
   b) comparing residues 2 through 35 of the N' terminal residues of the predicted protein against a Tat signal sequence motif, wherein the sequence motif is identified as $(X^{-1})R^{o}R^{+1}(X^{+2})(X^{+3})(X^{+4})$, wherein $X^{-1}$ is selected from the amino acid group consisting of M, H, A, P, K, R, N, T, G, S, D, Q and E;
   $R^{o}R^{+1}$ represent twin arginine residues, wherein $X^{+2}$ is selected from the amino acid group consisting of A, P, K, R, N, T, G, S, D, Q and E;
   $X^{+3}$ is selected from the amino acid group consisting of I, W, F, L, V, Y, M, C, H, A, P, N and T; and
   $X^{+4}$ is selected from the amino acid group consisting of A, Q, I, L, V, M and F;
   c) if the Tat sequence motif is identified, verifying an uncharged stretch of at least 13 amino acid residues in the 22 residues following twin arginines of the predicted protein;
   d) calculating the hydrophobicity sum of the first 13 residues of the uncharged region; verifying the hydrophobicity sum is a value less than 8.0; and
   if the motif is identified and the criteria c) and d) are met,
   e) identifying the predicted protein as a putative Tat substrate; and
   f) outputting amino acid sequence of the predicted protein to user.

2. The method of claim 1, wherein the predicted protein comprises known and recorded amino acid sequences of a polypeptide in a microorganism.

3. The method of claim 1, wherein the text file further comprises a file readable in FASTA format.

* * * * *

SEQUENCE LISTING

<160> NUMBER OF SEQ ID NOS: 7

<210> SEQ ID NO 1
<211> LENGTH: 6
<212> TYPE: PRT
<213> ORGANISM: asparagine
<220> FEATURE:
<221> NAME/KEY: MISC_FEATURE
<222> LOCATION: (1)..(6)
<223> OTHER INFORMATION: any amino acid

<400> SEQUENCE: 1

Xaa Arg Arg Xaa Xaa Xaa
1               5

<210> SEQ ID NO 2
<211> LENGTH: 38
<212> TYPE: DNA
<213> ORGANISM: Natronococcus sp.

<400> SEQUENCE: 2
gttagcacta agcttcgaaa ccgaattaaa atcattat                              38

<210> SEQ ID NO 3
<211> LENGTH: 35
<212> TYPE: DNA
<213> ORGANISM: Natronococcus sp.

<400> SEQUENCE: 3
cgagcgcagg acggtctttt tgtcgatacc cgccg                                 35

<210> SEQ ID NO 4
<211> LENGTH: 36
<212> TYPE: DNA
<213> ORGANISM: Natronococcus sp.

<400> SEQUENCE: 4
tcggcgggta tcgacaaaaa gaccgtcctg cgctcg                                36

<210> SEQ ID NO 5
<211> LENGTH: 30
<212> TYPE: DNA
<213> ORGANISM: Natronococcus sp.

<400> SEQUENCE: 5
gactgtggta cctcagtcgt cgtcggacag                                       30

<210> SEQ ID NO 6
<211> LENGTH: 38
<212> TYPE: DNA
<213> ORGANISM: Natronococcus sp.

<400> SEQUENCE: 6
gttagcacta agcttcgaaa ccgaattaaa atcattat                              38

<210> SEQ ID NO 7
<211> LENGTH: 30
<212> TYPE: DNA
<213> ORGANISM: Natronococcus sp.

<400> SEQUENCE: 7
gactgtggta cctcagtcgt cgtcggacag                                       30